US007949542B2

(12) United States Patent
Hamiter et al.

(10) Patent No.: US 7,949,542 B2
(45) Date of Patent: May 24, 2011

(54) SYSTEM, METHOD AND COMPUTER PROGRAM PRODUCT FOR GRAPHICALLY ILLUSTRATING ENTITIES AND GENERATING A TEXT-BASED REPORT THEREFROM

(75) Inventors: David M. Hamiter, Columbia, SC (US); Rodney V. Harrison, Columbia, SC (US); Stanley M. Hamiter, III, Lexington, SC (US)

(73) Assignee: Ionosoft, Inc., Columbia, SC (US)

( * ) Notice: Subject to any disclaimer, the term of this patent is extended or adjusted under 35 U.S.C. 154(b) by 1694 days.

(21) Appl. No.: 11/122,661

(22) Filed: May 5, 2005

(65) Prior Publication Data

US 2006/0262134 A1 Nov. 23, 2006

(51) Int. Cl.
*G06Q 50/00* (2006.01)
(52) U.S. Cl. ............................................. 705/2
(58) Field of Classification Search ................ 705/2
See application file for complete search history.

(56) References Cited

U.S. PATENT DOCUMENTS

| 5,798,766 | A  | * | 8/1998  | Hayashi et al. ............... 345/595 |
|-----------|----|---|---------|---------------------------------------|
| 5,920,317 | A  |   | 7/1999  | McDonald                              |
| 6,154,750 | A  |   | 11/2000 | Roberge et al.                        |
| 6,268,851 | B1 | * | 7/2001  | Bricklin et al. ............... 715/744 |
| 6,381,611 | B1 |   | 4/2002  | Roberge et al.                        |
| 6,516,220 | B2 |   | 2/2003  | Selvester et al.                      |
| 6,674,879 | B1 | * | 1/2004  | Weisman et al. ............ 382/128    |
| 6,735,272 | B1 |   | 5/2004  | Sorenson                              |
| 6,801,916 | B2 |   | 10/2004 | Roberge et al.                        |
| 7,793,217 | B1 | * | 9/2010  | Kim et al. ..................... 715/255 |
| 7,822,627 | B2 | * | 10/2010 | St. Martin ........................ 705/3 |
| 2001/0051881 | A1 |   | 12/2001 | Filler                              |
| 2002/0111932 | A1 |   | 8/2002  | Roberge et al.                      |
| 2002/0190980 | A1 |   | 12/2002 | Gerritsen et al.                    |
| 2003/0050801 | A1 |   | 3/2003  | Ries et al.                         |
| 2003/0120517 | A1 |   | 6/2003  | Eida et al.                         |
| 2003/0206169 | A1 | * | 11/2003 | Springer et al. .............. 345/442 |
| 2004/0015778 | A1 |   | 1/2004  | Britton et al.                      |
| 2004/0083217 | A1 |   | 4/2004  | Brackett et al.                     |
| 2004/0171955 | A1 |   | 9/2004  | Morganroth                          |
| 2005/0128211 | A1 | * | 6/2005  | Berger et al. ................ 345/582 |
| 2005/0137907 | A1 | * | 6/2005  | Barski et al. .................... 705/2 |

OTHER PUBLICATIONS

Irrgang, Menzel, and Kalmar. "New nomenclature and computerized programme of graphics for the description and recording of aortocoronary bypasses", European Journal of Cardio-Thoracic Surgery: 1991, 5:498-502.*

* cited by examiner

*Primary Examiner* — Dilek B Cobanoglu
*Assistant Examiner* — Robert Sorey
(74) *Attorney, Agent, or Firm* — Alston & Bird LLP

(57) ABSTRACT

A computer-implemented method for graphically illustrating an entity and generating a text-based report therefrom includes providing a visual base representation of an entity. The base representation includes a plurality of elements at least one of which is modifiable, where the elements are each associated with a plurality of attributes. A visual diagram of a particular entity is built based upon the base representation of the entity. In this regard, at least one visual element is added to the base representation, where the added visual elements are modifiable. Accordingly, the diagram includes the elements of the base representation and the elements added to the base representation. After determining attributes associated with the added elements, a text-based report is generated from the diagram, where the report is generated based upon the elements of the diagram and the associated attributes, and where the report is automatically generated from the diagram without user input.

33 Claims, 15 Drawing Sheets

LM: The Left Main is of a large caliber and is short. This vessel bifurcates into the left anterior descending and left circumflex systems. There exists a 90% ostial stenosis within this vessel.

LAD: The Left Anterior Descending is a medium caliber vessel. There is an 80% concentric stenosis located in the proximal segment, and a 90% tubular stenosis exists within the mid segment of this vessel. Mild irregularities exist within the mid and distal segment of this vessel.
The 1st Diagonal, which arises from the proximal segment, is a large caliber branch. There is a 60% eccentric stenosis located in the proximal segment of this branch.
The 1st Septal Perforator, arising from the mid segment, is of a small caliber. This branch is normal in its appearance.
The 2nd Diagonal, which arises from the mid segment, is of a small caliber. There exists a 70% ostial stenosis within this branch.

Cx: The Circumflex is a small caliber vessel. There are mild irregularities in the proximal, mid, and distal segment of this vessel.
The 1st Obtuse Marginal, arising from the proximal segment, is of a small caliber. There is a 2mm X 18mm drug eluting stent located in the proximal and mid segment of this branch. There is a 45% eccentric in-stent re-stenosis located in the proximal segment of this branch.
The 2nd Obtuse Marginal, which arises from the mid segment, is of a large caliber. There exists a 90% ostial stenosis within this branch. Mild irregularities exist within the proximal, mid, and distal segment of this branch.

RCA: The Right Coronary Artery is a medium caliber vessel and is dominant. A 90% concentric stenosis exists within the distal segment of this vessel. There are mild irregularities in the proximal, mid, and distal segment of this vessel.
The SinoAtrial, which arises from the proximal segment, is a small caliber branch. This branch appears normal.
The 1st Right Ventricular, arising from the mid segment, is of a small caliber. This branch appears normal.
The 2nd Right Ventricular, which arises from the mid segment, is of a small caliber. This branch appears normal.
The Posterior Descending Artery, which arises from the distal segment, is a medium caliber branch. This branch appears normal.

BYPASS GRAFTS:

Graft to mid LAD: An arterial graft, with ectasia in its proximal, mid, and distal segment, connects to the mid segment of the LAD.

Graft to mid 1st Diag: There is a venous graft, with a 90% ostial stenosis, connecting to the mid third of the 1st Diag.

Graft to proximal 2nd OM: There is a venous graft, which is patent, connecting to the proximal third of the 2nd OM.

Graft to mid PDA: A venous graft, with a 90% anastomotic stenosis, connects to the mid segment of the PDA.

FIG. 15.

SYSTEM, METHOD AND COMPUTER PROGRAM PRODUCT FOR GRAPHICALLY ILLUSTRATING ENTITIES AND GENERATING A TEXT-BASED REPORT THEREFROM

FIELD OF THE INVENTION

The present invention relates generally to systems and methods for graphically illustrating entities and generating text-based reports associated with the illustrated entities and, more particularly, relates to systems and methods for graphically illustrating entities, such as bodily organs, and automatically generating text-based reports therefrom.

BACKGROUND OF THE INVENTION

In various industries, one or more entities are analyzed or otherwise examined, after which a report is generated to memorialize the entity and the examination thereof. In the medical industry, for example, physicians and/or other medical personnel often examine bodily organs, and thereafter generate a report memorizing the bodily organ and their examination thereof. These reports can then be used, such as by the same or other medical personnel, for a number of different purposes including medical diagnosis, treatment, or the like.

As will be appreciated, in many instances, generating a report from the examination of an entity often includes the generation of graphical data acquired during or after examination of the entity, the graphical data being representative of portions or all of the entity. Thereafter, text-based information describing or otherwise interpreting portions of the entity are generated from the graphical data. For example, in performing a cardiac catheterization procedure, graphical data of a patient's heart is often acquired, and thereafter converted into a text-based report so that medical personnel anywhere can read and understand the interpretation of that graphical data. In this regard, cardiac catheterization reports typically include a number of different pieces of information related to the heart including, for example, an indication of each significant anatomical feature, each anatomical variant, each aberration due to a disease process, each stent present or required, and each by-pass graft that is present or required on the heart.

In the medical industry, a number of different techniques have been developed to generate a report based upon the examination of a bodily organ, such as the heart. In accordance with one of the more common techniques, referred to as the dictation technique, after acquiring or otherwise receiving images of an examined organ, a physician reviews the images and dictates information related to the organ into a voice capture device. To assist in dictating information related to the organ, the physician will often sketch portions of the images of the organ on a progress note along with a longhand summary of the physician's examination of the organ. Once the physician has dictated information related to the organ, the information is transcribed and formatted into a report, such as by a transcriptionist who must login to a secure voice recording system to access the physician's dictation. Thereafter, the physician must typically review and sign-off on the transcribed, formatted report to thereby formalize the report and end the physician's responsibility with respect to the report.

The dictation technique is adequate for examining a bodily organ and generating a report therefrom. As will be appreciated by those skilled in the art, however, the dictation technique has a number of drawbacks. In this regard, by requiring a number of different tasks, some of which are performed by different entities, the dictation technique can require an undesirably long time to formalize, typically from 48 hours or more. Also, whereas sketching portions of the images of the organ and preparing a longhand summary help the physician organize their thoughts before or as the physician dictates information related to the examined organ, such preparation also further adds time to that required to formalize the report.

In an effort to overcome a number of the drawbacks of the dictation technique, a number of different software packages have been developed to decrease the number of different tasks and time required to complete a report. In addition, a number of these software packages employ visual representations of portions of the human anatomy that, along with the completed report, better memorialize the examination of a bodily organ. One particular software package for generating a report based upon examination of a bodily organ is distributed by Cyberpulse™ Clinical Knowledge Systems. The Cyberpulse™ software package itself includes a drawing portion and a text-based reporting portion that are capable of generating a report based upon "drop-down" menus of notes to include in the drawing portion or phrases to include in the text-based reporting portion. In operation, a physician reviews images of an examined bodily organ and sketches elements of the organ to include in a report, or communicates those elements to a software technician. Using the Cyberpulse™ software package, the technician creates a drawing of the examined organ based upon the physician's sketches by selecting a "best fit" static graphic representation from a template library of graphic representations, and thereafter stacking static elements on top of that graphic representation to form a representation of the organ. The technician then selects various phrases to include in the text-based reporting portion, with the drawing of the examined organ and text-based reporting portion forming a report of the examined organ. Then, after reviewing the report, the physician signs-off on the report to thereby formalize the report and end the physician's responsibility with respect to the report.

Whereas software packages such as the Cyberpulse™ software package overcome drawbacks of the dictation technique, these software packages also have drawbacks. In this regard, many software packages for generating reports are too complex for a physician to utilize without the aid of a technician. Also, because creating a drawing and report requires navigating screen after screen, and from one set of menus to another, the actual time required to generate a report can be two to three times longer than the time required to transcribe a physician's dictation in the dictation technique. In addition, the graphical representation and reports generated by software packages such as Cyberpulse™ may be less customized for a particular patient or organ examination since the graphic and report elements are all pre-formed and simply dropped into the final graphic and report, respectively. In fact, elements that vary greatly in their appearance may not even be visually represented on the graphical representation, instead being represented as a text-block placeholder for their location. Further, the sketches and other information supplied by the physician may be too vague or otherwise misunderstood by a technician, or may even misrepresent the desired anatomical region, thereby resulting in a faulty report with a number of errors. Such a report may then be rejected by the physician upon review, forcing the physician and technician to resolve the errors in the report, or worse yet, inadvertently signed-off on by the physician.

SUMMARY OF THE INVENTION

In light of the foregoing background, embodiments of the present invention provide an improved system, method and computer program product for graphically illustrating entities and generating a text-based report therefrom. In accordance with embodiments of the present invention, a visual diagram of an entity can be created from a base representation of the entity to which elements may be added. In contrast to software packages such as Cyberpulse™, however, portions of the base representation, as well as one or more of the elements added thereto, may be modified or otherwise manipulated to thereby more accurately illustrate the entity represented by the diagram created therefrom. Accordingly, the diagram may be created without a library of templates illustrating various configurations of the diagrammed element. Further, as elements may be added to the base representation and thereafter modified such as by repositioning or reshaping the element on-the-fly, embodiments of the present invention capture a more accurate and detailed depiction of such elements than would otherwise be achieved by pre-formed elements.

As and/or after the diagram is created, embodiments of the present invention are also capable of dynamically and automatically creating a text-based report from the diagram. Advantageously, the report can be generated in a manner independent of or otherwise without user input other than that provided in creating the diagram. Also, the report can be generated by building language strings around attributes of the elements of a diagram, thereby resulting in a more natural language report than would otherwise be generated based upon pre-formed elements that are merely dropped into the report.

According to one aspect of the present invention, a computer-implemented method is provided for graphically illustrating an entity, such as a heart, and generating a text-based report therefrom. The method includes providing a visual base representation of an entity. The base representation includes a plurality of elements at least one of which is modifiable, where the elements are each associated with a plurality of attributes. After providing the base representation, a visual diagram of a particular entity is built based upon the base representation of the entity. In this regard, building the diagram includes adding at least one visual element to the base representation, where the added visual elements are modifiable. For example, when the entity comprises a heart, at least one vascular object can be added to a base representation of the heart, where the objects represent branches, grafts and/or collaterals. Additionally or alternatively, at least one modifier depending from at least one vascular object can be added, where the modifiers represent stents and/or aberrations.

The diagram therefore comprises the elements of the base representation and the elements added to the base representation. As or after elements are added to the base representation, attributes that are associated with each element added to the base representation are determined. For example, values for a position attribute, a length attribute and an angle attribute associated with an element can be determined for that element. The position, length and angle attributes thus define a direction of the element. A name attribute associated with the element can thereafter be determined based upon the direction of the element and at least one rule. Irrespective of the particular attributes of the elements, a text-based report is thereafter generated from the diagram, where the report is generated based upon the elements of the diagram and the attributes associated with the elements of the diagram, and where the report is automatically generated from the diagram without user input.

For at least one element of the diagram, the method can further include manipulating the shape and/or placement of the element on the diagram, and thereafter changing at least one attribute associated with the element based upon the manipulation. And as will be appreciated, the shape and/or placement can be manipulated, and the attributes changed, at one or more instances before generating the text-based report. For example, a shape can be manipulated by increasing or decreasing a curvature of the element, which may include increasing/decreasing the length and/or the direction of the element. More particularly, for example, an element can include a number of constantly-spaced points along its length, where each point is associated with a value representing a percent of the point along the length. The shape of such an element can then be manipulated in such a manner that increases or decreases the length of the element such that the number of points along the length of the element increases or decreases to thereby maintain the constant spacing. Also in response to increasing or decreasing the length of the element, the value associated with at least one point changes to reflect a change in percent of the point along the length of the respective element.

The diagram can more particularly include at least one element (i.e., child element) depending from at least one other element (i.e., parent element). An element can therefore be added to the diagram by selecting a visual element from a menu, and dragging the selected element from the menu to a stage including the base representation. The dragged element can then be dropped onto the stage, and snapped to an element from which the selected at least one element depends. In various instances, the elements include at least one visual object and at least one visual modifier depending therefrom. In such instances, a modifier can be added to the base representation by snapping the modifier to an object from which the modifier depends, where the object includes a plurality of points along its length, and proximate each of its sides. The shape of the modifier can then be framed by a series of consecutive points of the object such that a stock visual representation of the modifier is thereafter fit to the series of consecutive points framing the shape of the modifier to thereby form-fit the modifier to the object.

Before snapping a child element to its parent, a snap-to point of an element can be determined from a plurality of points along a length of each of one or more elements (e.g., neighboring elements) on the diagram. In this regard, the snap-to point can be determined based upon at least one predefined characteristic restrictions imposed by the selected element. An angle attribute of the child element can also be determined such that a side of the parent to which the child element snaps can be determined. Thereafter, the selected element can be snapped to the determined snap-to point, such as in a manner proximate the determined side of the parent so that the child element extends from the determined side.

When a parent element is manipulated in such a manner that increases or decreases the length of the element, the percent value associated with the snap-to point can be reassigned to a given point to reflect a change in percent of the snap-to point and the given point along the length of the respective element. Accordingly, the child element can be reassigned from the snap-to point to the given point, with the given point thereafter being the snap-to point of the child element.

The elements of the diagram can include elements of a plurality of different element types. Thus, to facilitate generating the text-based report, each element of the diagram can be assigned to a respective holder array, where each holder array includes an identifier for each element assigned to the holder array, and the identifier is linked to the attributes associated with a respective element. The text-based report can thereafter be generated based upon the holder arrays and the attributes linked to the element identifiers in the holder arrays.

More particularly, the text-based report can be generated by examining each element following a nested hierarchical ordering. One or more language strings can then be assigned for each element and associated attribute based upon the examination. For example, one or more supporting words can be placed before and/or after an attribute to thereby assign a language string to that attribute. After assigning the language strings, the text-based report can be generated based upon the language strings. For example, the language strings can be compiled into sentences, and thereafter ordered and concatenated into the text-based report. In various instances, compiling the language strings includes applying one or more functions to thereby increase grammatical accuracy of the sentences.

According to other aspects of the present invention, a system and computer program product are provided for graphically illustrating at least one entity and generating a text-based report therefrom. Therefore, embodiments of the present invention provide an improved system, method and computer program product for graphically illustrating entities and generating a text-based report therefrom. As indicated above, and explained below, the system, method and computer program product of embodiments of the present invention solve the problems identified by prior techniques and provide additional advantages.

BRIEF DESCRIPTION OF THE DRAWINGS

Figure 1:
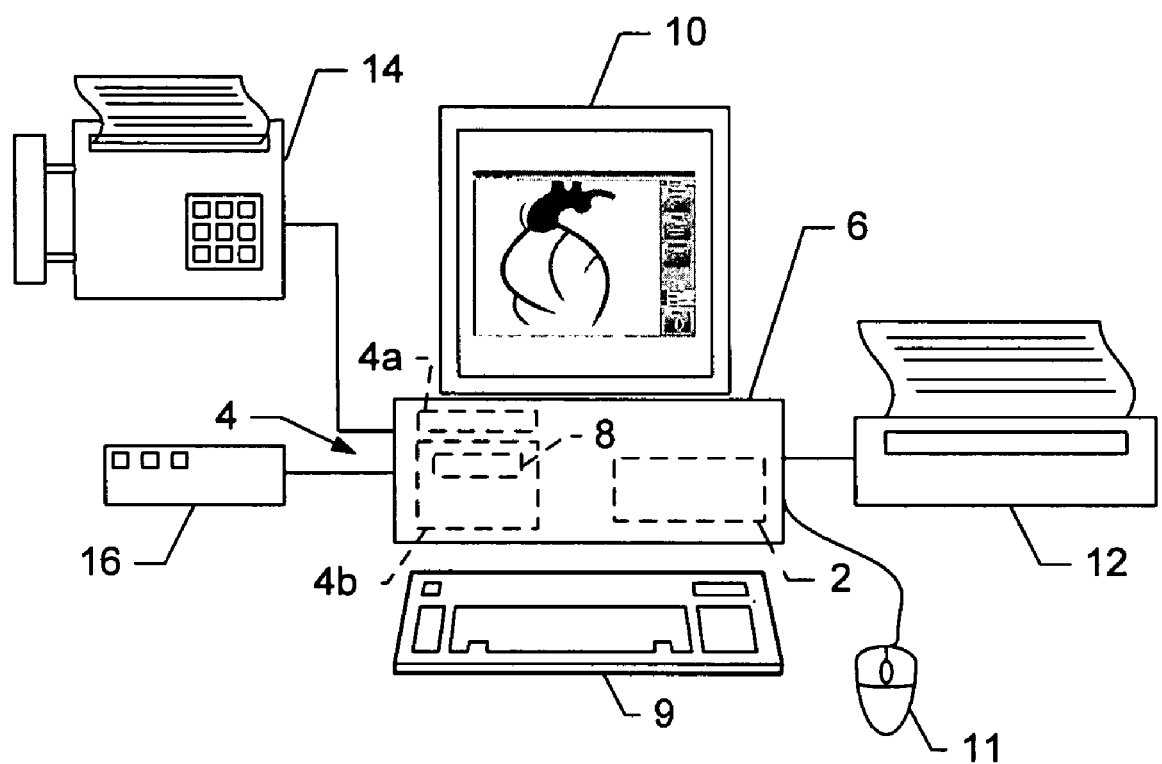
Figure 2:
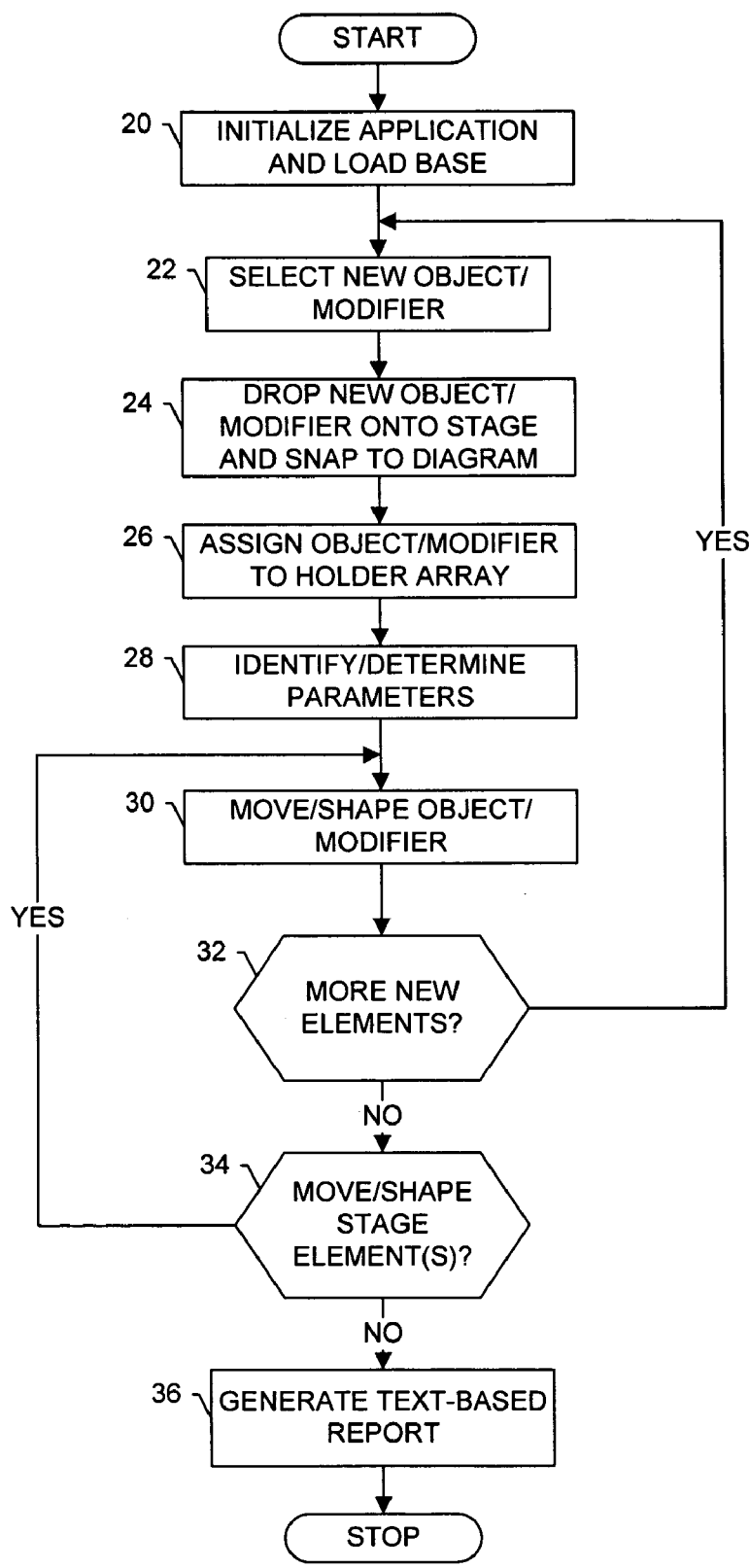
Figure 3:
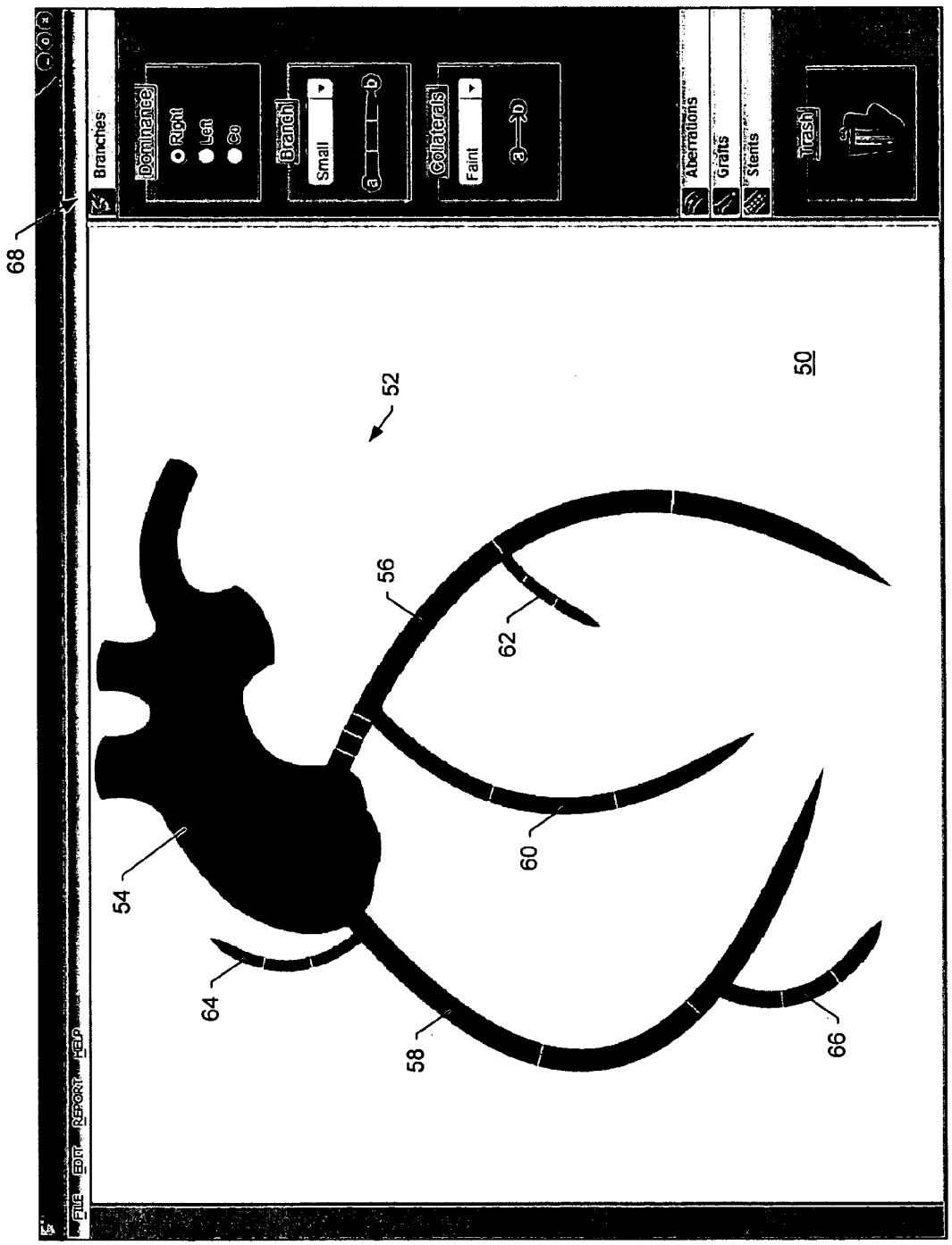
Figure 6A:
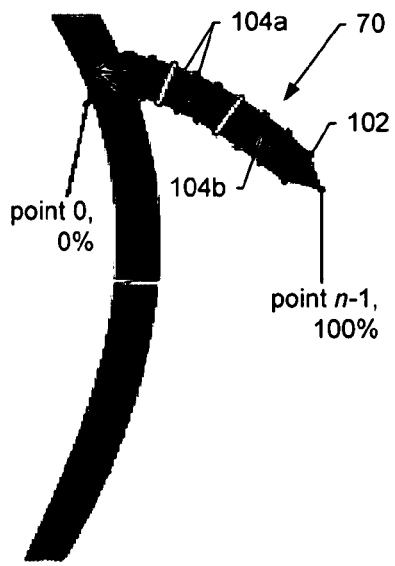
Figure 6B:
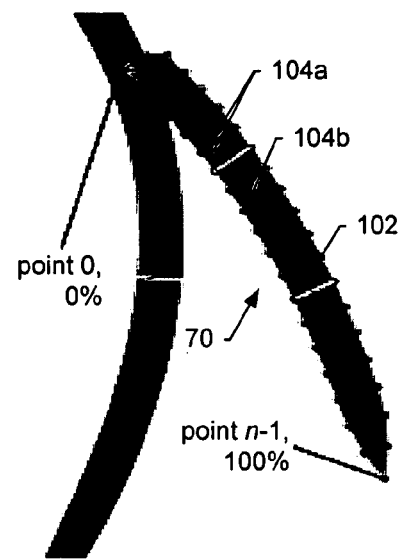
Figure 6C:
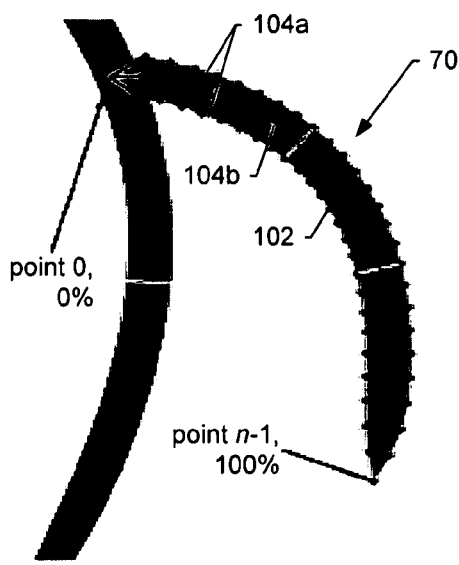
Figure 7:
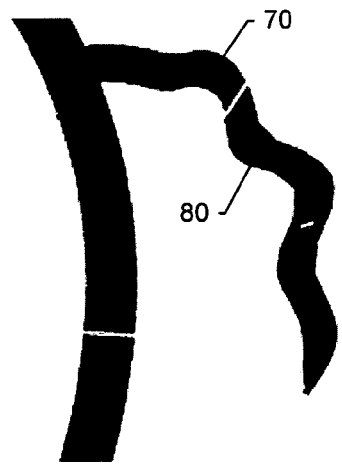
Figure 8A:
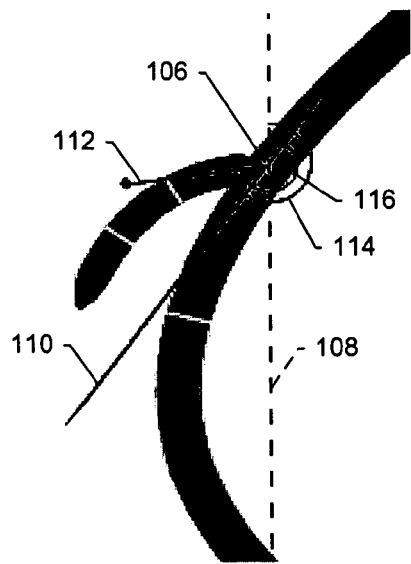
Figure 8B:
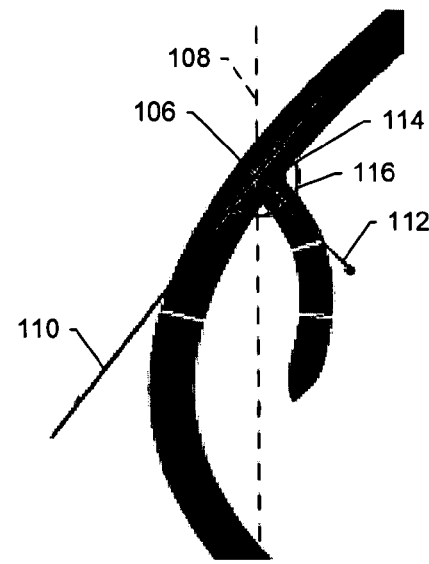
Figure 8C:
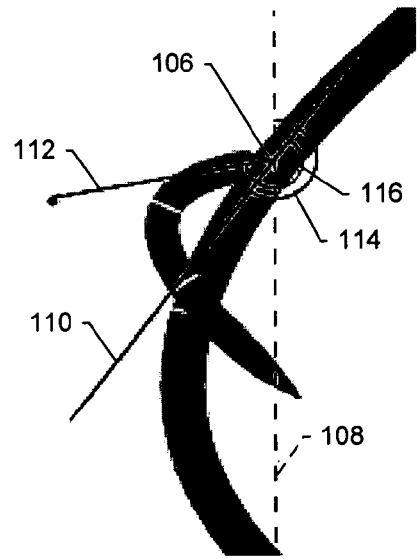
Figure 9A:
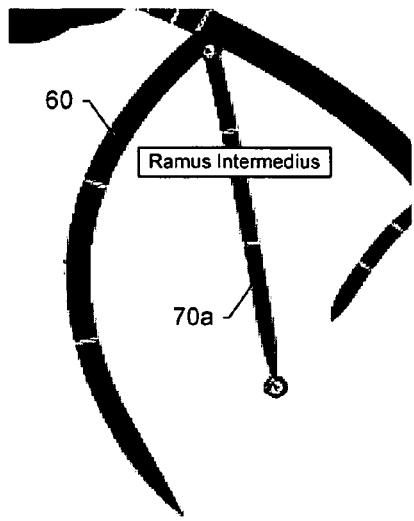
Figure 9B:
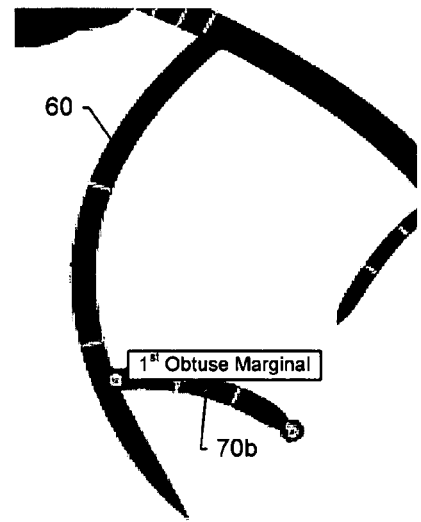
Figure 9C:
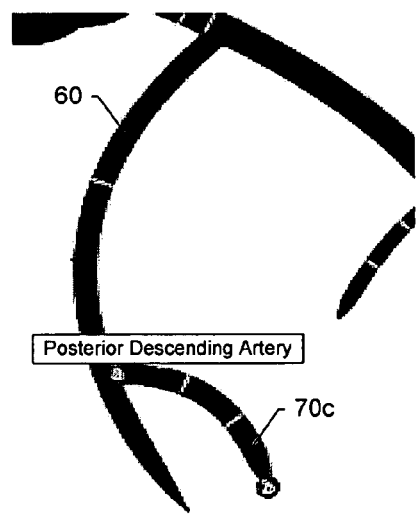
Figure 10:
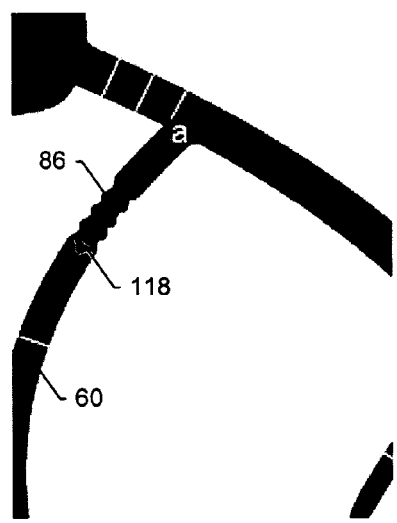
Figure 12:
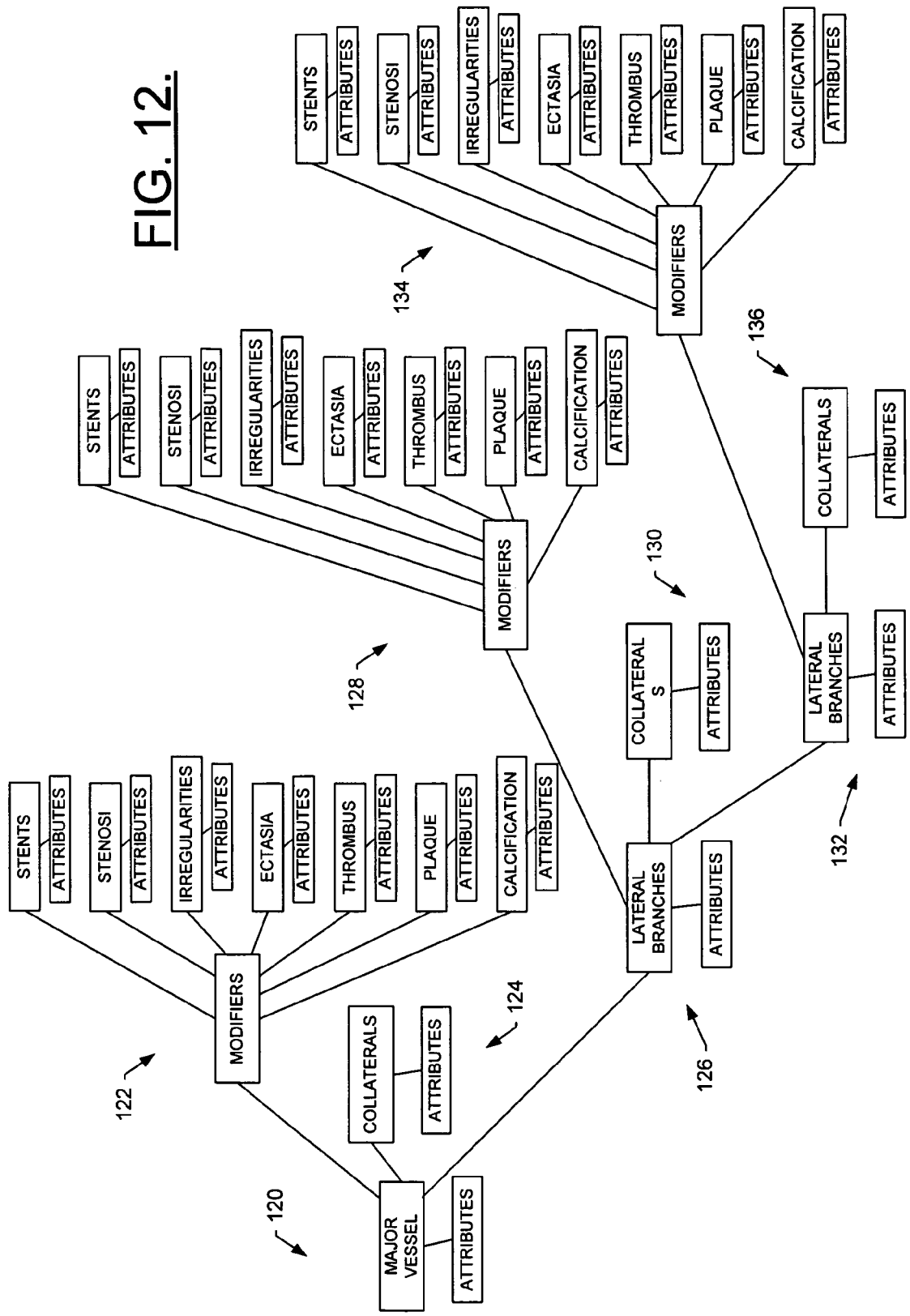
Figure 13:
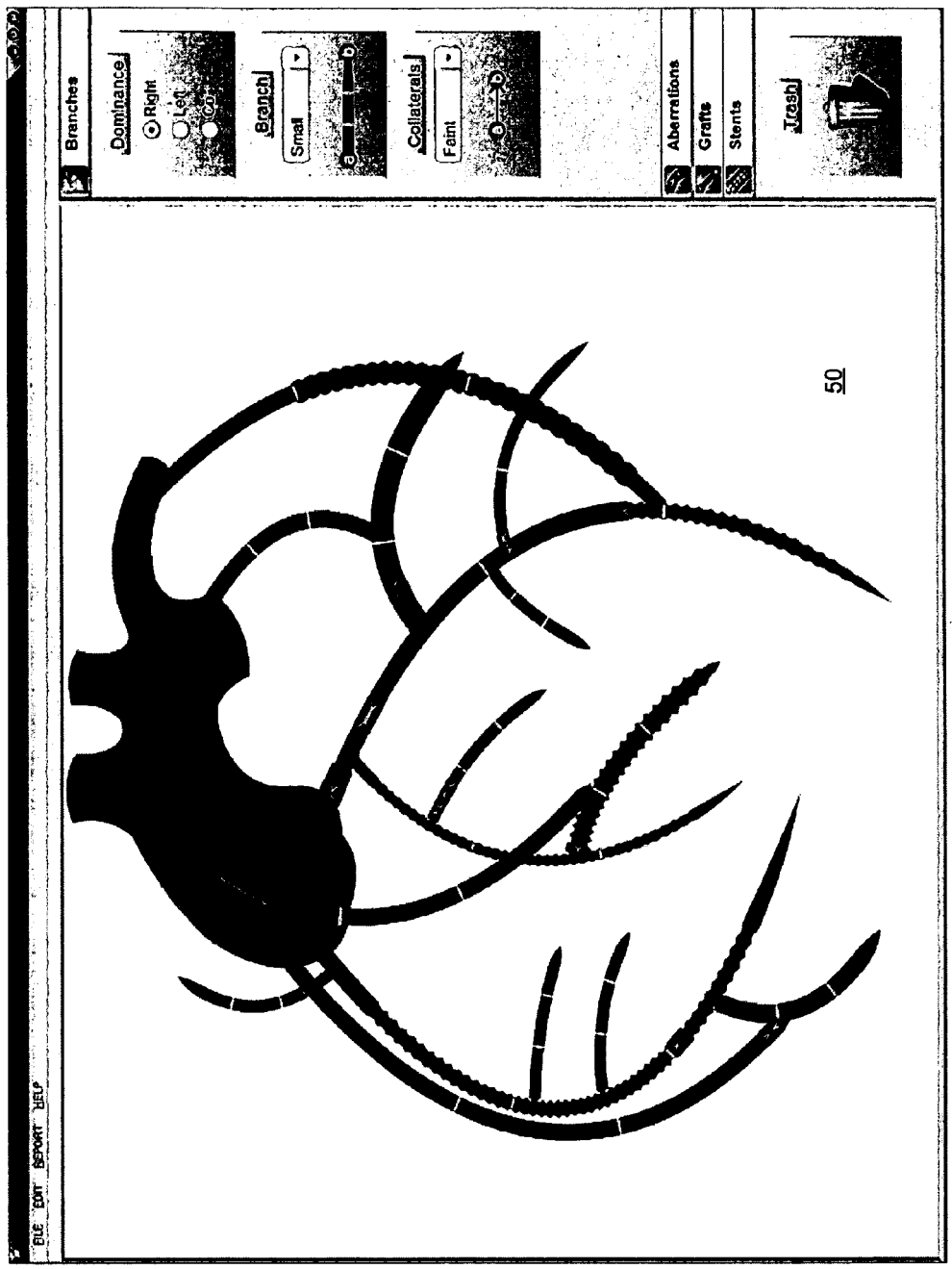
Figure 14:
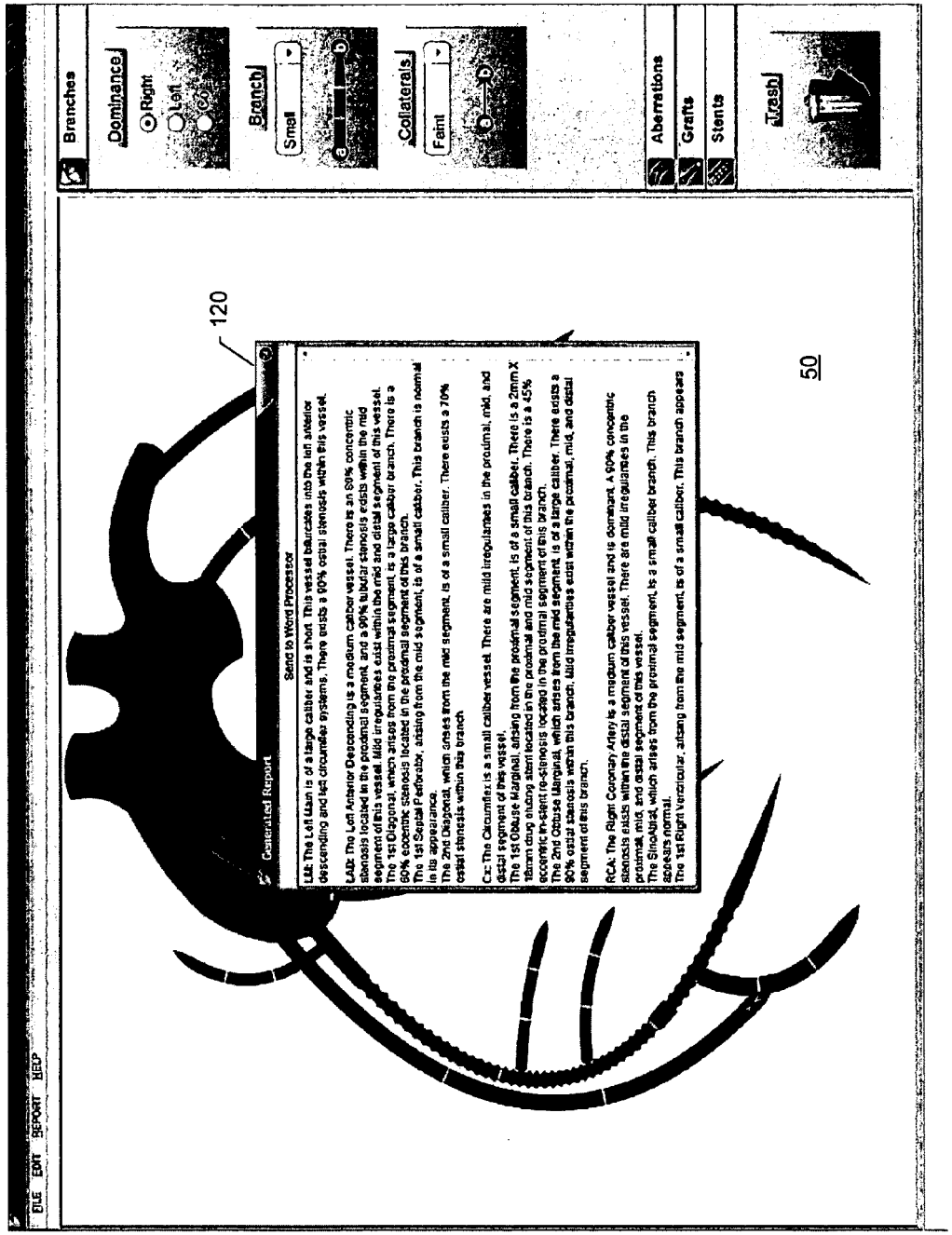

Having thus described the invention in general terms, reference will now be made to the accompanying drawings, which are not necessarily drawn to scale, and wherein:

FIG. 1 is a schematic block diagram of a system for graphically illustrating entities and generating a text-based report therefrom in accordance with one embodiment of the present invention embodied in a computer;

FIG. 2 illustrates various steps in a method of graphically illustrating an entity and generating a text-based report therefrom, in accordance with one embodiment of the present invention;

FIG. 3 is an exemplary display presented following initialization of a visual reporting application, including loading a base representation of an entity on a stage of a graphical user interface (GUI) of the application, in accordance with embodiments of the present invention;

FIGS. 4a-4e are exemplary menus presented by the GUI of the visual reporting application for selecting elements to add to the base representation shown in FIG. 3, in accordance with embodiments of the present invention;

FIGS. 5a-5d are schematic diagrams illustrating a technique for drawing an object including applying curved gradient color fills, in accordance with embodiments of the present invention;

FIGS. 6a-6c are schematic diagrams illustrating a vascular object being formed of a number of points, where the number of points may change as the object is stretched, bent or otherwise re-shaped, in accordance with embodiments of the present invention;

FIG. 7 is a schematic diagram illustrating a branch object having an associated tortuosity attribute;

FIGS. 8a-8c are schematic diagrams illustrating a technique for determining angle attributes of a vascular object, in accordance with embodiments of the present invention;

FIGS. 9a-9c are schematic diagrams illustrating a technique for determining a name attribute of a vascular object, in accordance with embodiments of the present invention;

FIG. 10 is a schematic diagram illustrating a technique for altering a length attribute of a dependent modifier, in accordance with embodiments of the present invention;

FIGS. 11a-11d are schematic diagrams illustrating reshaping an object of the diagram, in accordance with one embodiment of the present invention;

FIG. 12 is a flow diagram of objects and modifiers of a graphical diagram followed during examination of the objects and modifiers to thereby generate a text-based report from the diagram, in accordance with embodiments of the present invention;

FIG. 13 is an exemplary display including a diagram built from the base representation shown in FIG. 1, in accordance with embodiments of the present invention;

FIG. 14 is an exemplary display illustrating a text-based report generated based upon the diagram of FIG. 13, in accordance with embodiments of the present invention; and FIG. 15 is an exemplary display illustrating the text-based report of FIG. 14 as such may be presented by a word processing application, in accordance with embodiments of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The system, method and computer program product according to embodiments of the present invention are capable of graphically illustrating entities and generating a text-based report therefrom. In this regard, the software application can comprise any of a number of different software applications capable of operating on a processing element, such as a personal computer, a network appliance, a server computer or the like. The software application is also typically capable of presenting one, or more typically, a plurality of displays to a user, such as during installation, initialization and/or operation of the software application. The displays are presented via a graphical user interface (GUI) and include content organized such that information required for the system to perform a task may be spread across a plurality of displays.

Generally, the system, method and computer program product of embodiments of the present invention permit a user to graphically illustrate an entity by dragging graphical elements of that entity onto a stage, and manipulating their positions and shapes by dragging control points. This intuitive, visual approach requires little, if any, specialized knowledge aside from that required to operate a personal computer. The system, method and computer program product of embodiments of the present invention utilize vector-based graphics, such as scalable vector graphics (SVG), rather than bitmaps or other raster-based image formats. Consequently, the quality of the rendered images is consistent, regardless of scale or resolution. Elements of an entity can be programmatically drawn on-the-fly such that the system, method and computer program product of embodiments of the present invention are independent of, or otherwise are not dependent on, static images or templates. This flexibility lends itself considerably to accurately depicting virtually any variance or anomaly in graphically representing an entity and its elements. Further, by providing a system, method and computer program product operable independent of a library of static images or templates, embodiments of the present invention require less storage than other, conventional techniques for graphically illustrating similar entities.

As shown in FIG. 1, the system of one embodiment of the present invention is typically embodied by a processing element 2 and an associated memory device 4, both of which are commonly comprised by a computer 6 or the like. The memory device can comprise any of a number of known memory devices, such as random access memory (RAM) 4a and/or a non-volatile storage device 4b. The non-volatile storage device, such as, for example, flash memory, an EEPROM or a disk, is typically used for storing a visual reporting application 8, as well as storing useful data such as, for example, configuration settings required for operation of the visual reporting application, and/or one or more reports generated by the visual reporting application, as described below. Further, the RAM is generally used for loading and executing the visual reporting application, and for storing various pieces of data during execution of the visual reporting application.

The computer 6 can include a display 10 for presenting information, such as operational displays of the visual reporting application 8, in accordance with embodiments of the present invention. The computer can also include a user input interface which, in turn, can include a keyboard 9, keypad or the like. Additionally or alternatively, the user input interface can include a pointing device 11, such as a mouse, trackball, touchpad, or touch screen (may be integrated into display). To plot information, such as the information presented by the display unit, the computer can further include a printer 12. Also, the computer can include a means for locally or remotely transferring information, such as the information presented by the display unit and/or plotted by the printer. For example, the computer can include a facsimile machine 14 for transmitting information to other facsimile machines, computers or the like. Additionally, or alternatively, the computer can include a modem 16 to transfer information to other computers or the like. Further, the computer can include an interface (not shown) to a network, such as a local area network (LAN) and/or a wide area network (WAN). For example, the computer can include an Ethernet Personal Computer Memory Card International Association (PCM-CIA) card configured to transmit and receive information to and from a LAN, WAN or the like.

As will be appreciated, and as described below, the visual reporting application 8 need not be stored by the non-volatile storage device 4b. In this regard, the visual reporting application can be stored on another processing element, such as another personal computer or server computer, in either wireless or wireline electrical communication with the computer 6, such has via a common network. In such instances, the computer may be capable of remotely accessing and operating the visual reporting application from the other processing element. For example, the visual reporting application can reside on a network server, rather than on users' personal computers (computer 6). Each of the users' computers, then, can include another software application, such as a Web browser, that allows the respective computer to connect to the server to access the visual reporting application.

Reference is now made to FIG. 2, which illustrates various steps in a method of graphically illustrating an entity and generating a text-based report therefrom, in accordance with one embodiment of the present invention. As used herein, embodiments of the present invention will be shown and described as graphically illustrating a bodily organ such as the heart and generating a text-based report therefrom, such as in the context of cardiac catheterization and angiography modalities. It should be understood, however, that embodiments of the present invention may be equally applicable in any of a number of other medical contexts to image one or more organs, systems or the like of the body, such as with respect to ECHO (echocardiogram), nuclear medicine imaging, computed tomography or the like, without departing from the spirit and scope of the present invention. Further, it should be understood that embodiments of the present invention may be equally applicable in any of a number of non-medical contexts, without departing from the spirit and scope of the present invention.

For example, embodiments of the present invention may be applicable to graphically illustrating scenes of a story including characters, objects and any other scene elements, and generating a text-based story therefrom. Also, for example, embodiments of the present invention may be applicable to graphically recreating all or a portion of an entity (e.g., skeletal system, plant, etc.) from known portions of the respective elements (e.g., discovered skeletal fragments, plant leaves, etc.), and generating a text-based report identifying a type of the respective entity (e.g., species type) from an analysis of the recreated portion of the entity. Further, for example, embodiments of the present invention may be applicable to constructing molecular models, tracking/reporting pollutant strength within rivers and sub-streams, tracking/reporting a medium (e.g., fluid/gas/aerosol) pressure and/or volume as the medium traverses a complex constrained system (e.g., piping), tracking/reporting weather, palm reading, object identification, evolution games, or the like.

A. Creating a Graphical Illustration/Diagram of an Entity

As shown in block 20 of FIG. 2, the method of one embodiment of the present invention includes initializing the visual reporting application 8. Upon initialization, the application presents a GUI that includes a stage 50, which is loaded with a base representation of the entity. For example, as shown in the exemplary display of FIG. 3, the stage can be loaded with a base representation of the heart 52 that includes representations of the aorta 54 and a number of elements typically representing the fundamental branches of the heart that are common to most if not all humans. More particularly, for example, the base representation of the heart may include elements representing the left coronary artery 56, right coronary artery 58, circumflex 60, first septal perforator 62, sinoatrial 64 and/or posterior descending artery 66. As shown, elements referred to as being "left" appear to the right, while elements referred to as being "right" appear to the left. In this regard, it should be appreciated that the diagram appears from the user's point of view. The elements are named, however, from the element's point of view, which may be opposite the user's point of view. Also, unless otherwise noted, branches may refer to not only branches but may additionally or alternatively refer to vessels of the heart. Nonetheless, the left coronary artery, right coronary artery and circumflex may separately be referred to as vessels.

Generally, the visual reporting application 8 permits a user to build a diagram of the entity from the base representation 52 by deleting and/or manipulating the shape and/or placement of one or more elements of the base representation. In addition, building the diagram can include adding other elements to the base representation and, if so desired, manipulating the shape and/or placement of the added elements. More particularly with reference to a heart entity, the visual reporting application permits a user to build a diagram of a particular heart (see FIG. 13). For example, a user may build a diagram of a patient's heart to memorialize an examination of the patient, such as during a cardiac catheterization procedure.

Thus, when the entity comprises a vascular system such as the heart, the elements include, for example, the aorta 54, vascular objects, and modifiers dependent on vascular objects. Vascular objects can represent branches, grafts, and collaterals that are stretchable, bendable tube-like graphical structures that may be formed of a number of points, lines, Bezier curves or the like. Modifiers, on the other hand, represent stents or aberrations (e.g., stenosi, irregularities, ectasia, thrombus, ulcerated plaques, calcification, etc.) that appear, and are thus dependent, on vascular objects. In this regard, although collaterals may also be dependent on vascular objects, collaterals are more readily associated with vascular objects than modifiers. As shown and described herein, vascular objects and modifiers may depend from vascular objects. It should be understood, however, that various instances of one or more vascular objects may alternatively depend from the aorta. Thus, it should be understood that when an object is shown and/or described as depending from another object, that object may equally depend from the aorta, without departing from the spirit and scope of the present invention.

Figure 4A:
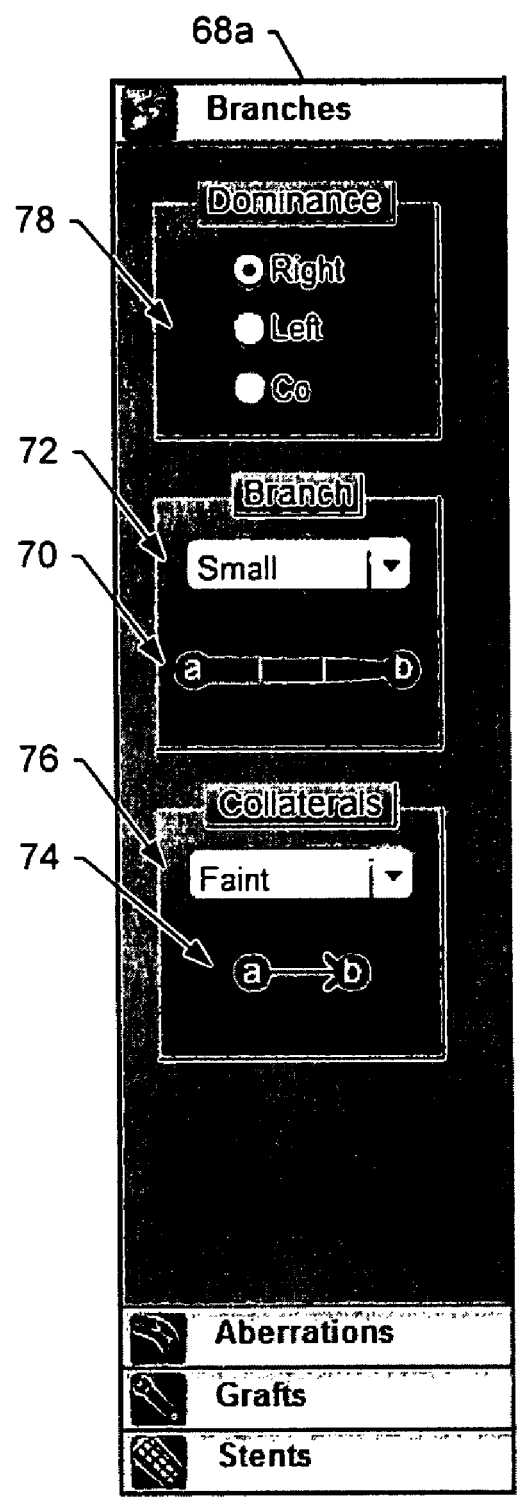

In accordance with embodiments of the present invention, elements can be added to, deleted from and/or manipulated within the stage 50 via a user interface pointer and a simple drag-and-drop interface. Accordingly, in one embodiment, the GUI of the visual reporting application 8 includes, in addition to the stage 50, one or more menus 68 from which a user can select vascular objects and modifiers with which to build the diagram. As shown in FIG. 3, and more particularly in the partial exemplary displays of FIGS. 4a-4d, the menus 68 provided by the visual reporting application GUI may permit the user to select elements and, if so desired, one or more attributes associated with respective elements. The menus, as shown, can be presented by the GUI in a tabular manner including, for example, a branches menu 68a, an aberrations menu 68b, a grafts menu 68c and a stents menu 68d. As shown in FIG. 4a, the branches menu can include a field for selecting a new branch 70 and an associated caliber 72 (e.g., small, medium, large), as well as a field for selecting a new collaterals 74 and an associated degree 76 (e.g., faint, moderate, heavy). In addition, the branches menu can include a field for selecting dominance 78 of the right coronary artery and circumflex (e.g., right, left, co-dominant), where the dominance attribute is based upon the location of the posterior descending artery or arteries 66.

Figure 4B:
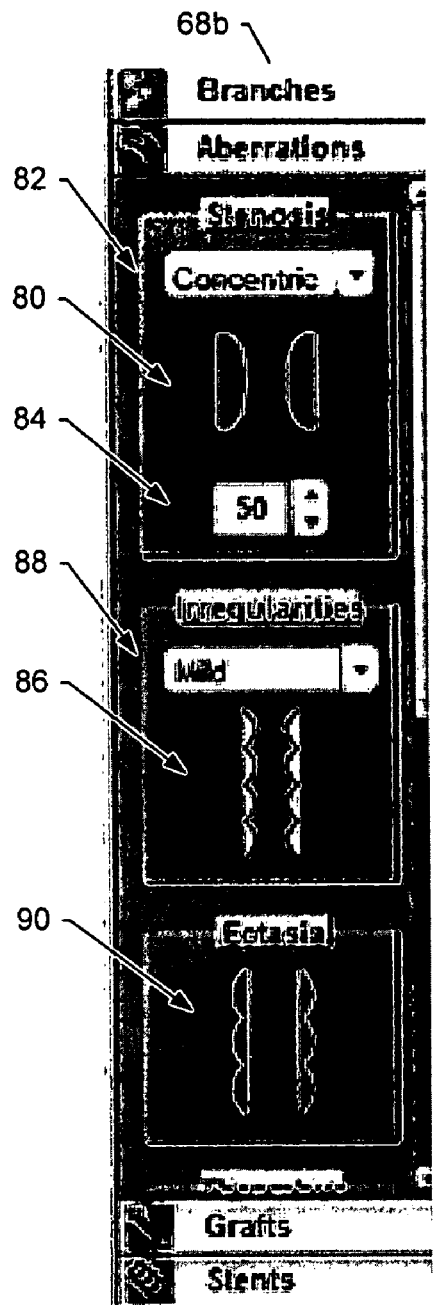
Figure 4C:
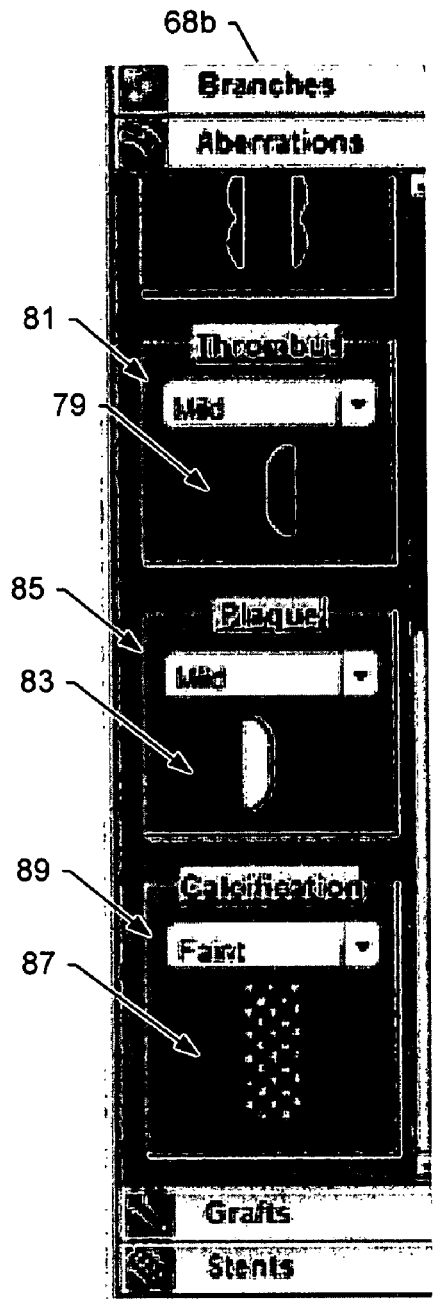
Figure 4D:
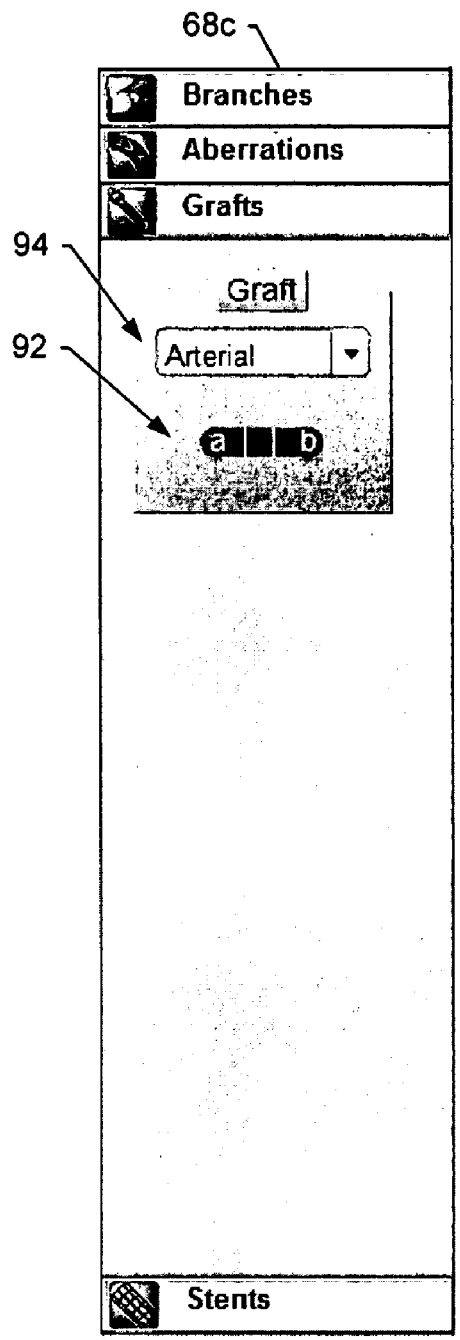
Figure 4E:
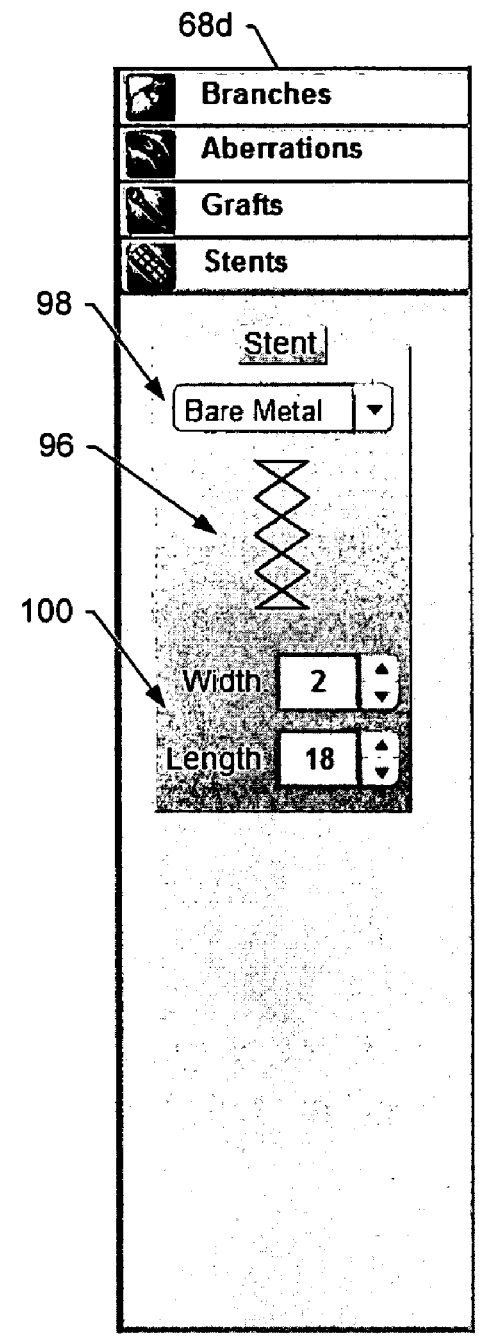

As shown more particularly in FIG. 4b, the aberrations menu 68b can include a field for selecting a new stenosis 80, including an associated type 82 (e.g., concentric, eccentric, ring, ostial, tubular, anastomotic) and degree or percentage of blockage 84. The aberrations menu can also include a field for selecting a new irregularity 86 and an associated degree 88 (e.g., mild, moderate, severe), and a field for selecting a new ectasia 90. In addition, as shown in FIG. 4c, the aberrations menu can include a field for selecting a new thrombus 79, including an associated degree 81 (e.g., mild, moderate, severe); selecting a new ulcerated plaque 83, including an associated degree 85 (e.g., mild, moderate, severe); and/or selecting a new calcification 87, including an associated degree 89 (e.g., faint, moderate, heavy). The grafts menu 68c can include a field for selecting a new graft 92 and an associated type 94 (e.g., arterial, venous, LIMA (left internal mammary artery), saphenous-vein), as shown in FIG. 4d. And as shown in FIG. 4e, the stents menu 68c can include a field for selecting a new stent 96 and an associated type 98 (e.g., bare-metal, drug-eluting), as well as an associated width and length 100.

Figure 5A:
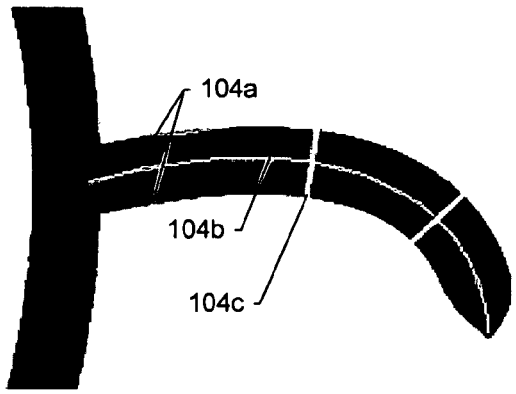
Figure 5B:
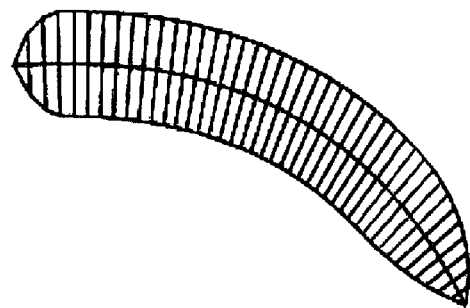

Vascular objects representing branches 70 (including the left coronary artery 56, right coronary artery 58, circumflex 60, first septal perforator 62, sinoatrial 64 and/or posterior descending artery 66 of the base representation 52) and/or grafts 94 are formed from a pair of sides 104a and a center 104b (or base-curve). Generally, each object has a "bent" symmetry such that the proximate center of a straight line 104c, drawn from one side of the object to the other side and perpendicular to the base curve, intersects the base curve, as shown in FIG. 5a with respect to a branch. To draw such objects from a frame of the sides and base curve, the frame is spliced into a plurality of symmetrical wedges, as shown in FIG. 5b with a reduced number of wedges for easier illustration. To splice the frame, the base curve can be approximated as an iterative (and, perhaps, compound) Bezier curve, with the coordinates of the points along that Bezier curve recorded for further processing. Because the base curve is comprised of a series of line segments, the number of points chosen determines the efficacy and resolution of the object, and as such, the number of points in one typical embodiment is at least half the distance of the approximated path of the base curve.

For each point along the Bezier curve approximating the base curve 104b, the average of the angles between the point and its two neighboring points along the base curve is found. The outline of the object can be comprised of twice as many points as were produced by our Bezier approximation. Accordingly, for each point on the base curve, corresponding outline points can be found by taking the sine and cosine of the Bezier point's angle (average angle), plus or minus 90°, and multiplying that value by half the object's width (from side 104a to side) at that iteration. From these contour points, a series of quadrilaterals can be constructed by connecting the corresponding points on either side of the shape.

Figure 5C:
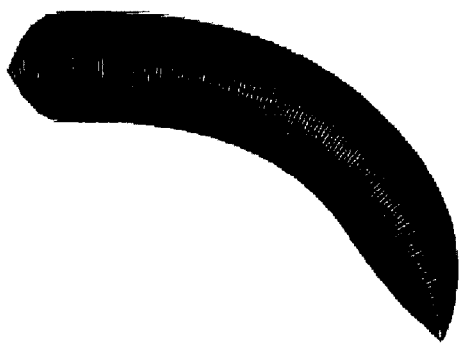
Figure 5D:

After constructing the quadrilaterals, each quadrilateral can be given a linear gradient fill at an angle matching that of the line segment running through the quadrilateral's center (belonging to the original Bezier curve approximating the base curve 104b). The coordinates, dimensions, colors, color ratios, and angle of the gradient can then be delivered and manipulated via a box type or 3×3 affine transformation matrix, as shown in FIG. 5c with a reduced number of wedges for easier illustration. As can be seen in FIG. 5d, the final object drawn by the visual reporting application 8 is generally a smooth, curved gradient fill that can be utilized to produce a number of effects that would not otherwise be possible with vector graphics.

As interpreted by the visual reporting application 8, vascular objects include a number of points. More particularly, as shown in FIGS. 6a-6c with respect to a branch, such vascular objects are formed of n uniformly-spaced points 102 along each of their sides 104a and down their center 104b (or their base-curve), ranging from point 0 at their origin to point n−1 where they taper and terminate. As described herein, the origin point of such an object may also be referred to as "control point A," while the termination point may be referred to as "control point B." The number of points n−1 (and hence the value of the end point) can be directly proportionate to the length of the vascular object, and can therefore adjust whenever the object is stretched, shrunk and/or curved, as explained below. At this point it should be noted that, for purposes of clarity, the number of points illustrated in FIGS. 6a-6c is a fraction (e.g., 20%) of the number of points typically forming such objects. It should also be noted that, although the visual reporting application 8 can interpret the points of such objects, the respective points are typically not visible to the user.

To maintain consistent, relative positioning of objects and modifiers dependant thereon, each point of each vascular object is associated with a value that represents the percent of that point along the length of the vascular object. As also shown in the exemplary displays of FIGS. 6a-6c, the range of percent values, then, can extend from 0% at point 0 to 100% at point n–1. As the object is stretched, shrunk and/or curved, the number of points may increase or decrease so as to maintain constant spacing between the points. Accordingly, the percent associated with each point may be reassigned upon stretching, shrinking and/or curving a vascular object such that a modification in the number of points can be reflected in the associated percent values.

The elements are each associated with a number of attributes including, for example, a name attribute, a position attribute, a length attribute, one or more angle attributes, and a parent attribute (indicating the element from which an element depends). As vascular objects such as grafts 92 and collaterals 74 may extend from one element (e.g., branch 70) to another element, such objects may have, in addition to a parent attribute, a target attribute that indicates the element and associated position to which the element extends. As indicated above with respect to the branches menu 68a of FIG. 4a, branches 70 are also typically associated with a caliber attribute, while the right coronary artery 58 and circumflex 60 are also typically associated with a dominance attribute. In addition, as shown in FIG. 7, branches may also be associated with a tortuosity attribute specifying a degree of tortuosity (bendedness, twistedness) along its length (e.g., at 0%, 33% or 66%), where the tortuosity attribute may comprise none, mild, moderate, or severe, for example. Further, with the exception of the circumflex 60, branches extending from another branch (referred to as the "parent" branch) are referred to as lateral branches and are also typically associated with an ordination attribute, which can be set to a first branch, second branch, third branch or the like. As will be appreciated, ordination of a lateral branch can supplement the branch's name to further specify lateral branches of the same type (e.g., having the same parent, direction of flow, etc.). Accordingly, for example, two lateral branches extending from the right coronary artery with the same direction of flow, which may have the same name attribute (explained below), may be distinguished based upon the ordination attribute (one branch being the first branch and the other being the second branch).

Elements such as stenosi 80, grafts 92 and/or stents 96 typically have an additional type attribute that supplements their respective names for further specificity. Stenosis types can include, for example, concentric, eccentric, ring, tubular, ostial or anastomotic, as indicated above with respect to the aberrations menu 68b of FIG. 4b. As indicated above with respect to the grafts menu 68c of FIG. 4d, for example, a graft may have an associated type of arterial, venous, LIMA or saphenous-vein. In addition, when two or more grafts are coupled together, the respective grafts may be treated as a single, complex graft, which is typically associated with a further type attribute set to either bifurcating or sequential depending upon the manner in which the grafts are coupled together. A stent, for example, may have an associated type of bare-metal and drug-eluting, as indicated above with respect to the stents menu 68d of FIG. 4e, and may also specify the stent manufacturer, if so desired.

As further indicated above with respect to the menus 68, elements such as collaterals 74, irregularities 86, stenosi 80, thrombus 79, ulcerated plaques 83 and calcification 87 are also typically associated with a degree attribute. More particularly, for example, collaterals and calcification may be associated with the degree of faint, moderate or heavy. Irregularities, thrombus and ulcerated plaques may be associated with the degree of mild, moderate or severe, for example. And a stenosis may be associated with a degree equaling its percent of blockage, which typically ranges from 1% to 100%. In this regard, when the degree of a stenosis equals 99%, the percent degree may further indicate that the degree represents a "sub-total" or "near-total" occlusion. Similarly, when the degree of a stenosis equals 100%, the percent degree may optionally further indicate that the degree represents a "total" occlusion. For a summary of various vascular objects and modifiers, and their associated attributes, see Table 1 below.

TABLE 1

| Element (basic attributes: name, position, length, angle, parent): | Additional Attributes: | Examples: |
| --- | --- | --- |
| Branches: | Caliber | Small, medium, large |
| Left/Right Coronary Artery/Circumflex | Caliber | Small, medium, large |
| | Dominance | Right, left, co-dominant |
| | Tortuosity | None, mild, moderate, severe |
| Lateral Branches | Caliber | Small, medium, large |
| | Ordination | First, second, third, etc. |
| | Tortuosity | None, mild, moderate, severe |
| Graft | Target | Target element, location |
| | Type | Arterial, venous, LIMA, saphenous-vein; and, for complex grafts, bifurcating, sequential |
| Collateral | Target | Target element, location |
| | Degree | Faint, moderate, heavy |
| Stent | Type | Bare-metal, drug-eluting and, of so desired, stent manufacturer |
| Stenosis | Type | Concentric, eccentric, ring, ostial, tubular, anastomotic |
| | Degree | Percent of blockage; and, optionally, "sub-total" or "near-total" occlusion for 99% blockage, or "total" occlusion for 100% blockage |
| Irregularities | Degree | Mild, moderate, severe |
| Thrombus | Degree | Mild, moderate, severe |
| Ulcerated plaque | Degree | Mild, moderate, severe |
| Calcification | Degree | Faint, moderate, heavy |

In operation, the visual reporting application 8 draws and/or re-draws vascular objects and modifiers as a consequence of the user adding those objects and modifiers to the stage 50 to thereby build a diagram. In addition, the application can draw and/or re-draw objects and modifiers as a consequence of the user repositioning, stretching and/or curving those objects and modifiers during the diagram build, and/or as a result of changes made to a vascular object upon which other objects and/or modifiers depend. Further, one or more vascular objects and modifiers can be drawn and/or re-drawn as a consequence of the user changing one or more attributes of the respective objects and modifiers during the diagram build, such as by means of a respective menu 68. As explained below, the visual reporting application 8 can identify vascular objects and modifiers by their anatomically correct names and attributes through an examination of the relationships between an object's position, angle/orientation, curvature, length, and hierarchy relative to the surrounding objects and modifiers that collectively form the diagram. As explained herein, then, such an examination may be referred to as geometric analysis conducted during the draw phase.

During the draw phase, after initializing the visual reporting application 8 and loading the base representation 52 onto the stage 50 of the application GUI (see FIG. 2, block 20), a vascular object or dependent modifier is selected, such as from a respective menu 68, as shown in block 22. Thereafter, the selected object or modifier can be placed or otherwise dropped onto the stage of the GUI, as shown in block 24. In this regard, a vascular object dropped onto the stage has an initial length (e.g., number of points) and shape including, as explained above, a control point A (i.e., origin point 102) and a control point B (i.e., termination point). The vascular object may be split into thirds along its length, where the segments may be separated from one another by thin lines, and may be referred to as the proximal, mid and distal segments from the origin point to the termination point, respectively. When a vascular object is dropped onto the stage, its control point A connects or otherwise snaps to a point relative to the closest anatomically feasible point along the base-curve 104b of another vascular object on the stage, such as an object of the base representation 52 or an object previously added to the base representation. The point to which the vascular object snaps being thereafter referred to as the "snap-to" point. The dropped object then effectively becomes the child of the now parent object to which the respective object snaps.

When a dependent modifier is placed or otherwise dropped onto the stage 50 of the GUI, the modifier has an initial length, as well as a control point that typically corresponds to the origin point 102 of the modifier. As with vascular objects, when a modifier is dropped onto the stage, its control point may connect or otherwise snap to a point relative to the closest anatomically feasible point along the base-curve 104b of a vascular object on the stage. The shape of the modifier may then be determined based upon a stock representation of the modifier, which may be altered based upon the modifier's length, and the width of the respective parent object (defining the modifier's width). More particularly, for example, the shape of a modifier can be framed by a series of consecutive points of the parent object including, for example, the snap-to point on one side 102a of the parent, the corresponding point on the opposite side, the point whose numerical value is the sum of the snap-to point and the modifier's length, the corresponding point on the opposite side, and all points in-between. The stock representation of the modifier can then be fit to the coordinates of the points framing the modifier to produce a refined set of coordinates that may be connected by lines, Bezier curves, and/or color fills to produce the dynamically generated modifier. In this way, the modifiers may be form-fitted to their parent vascular objects. Accordingly, when the parent vascular object is re-positioned or re-shaped, its dependant modifiers may also be re-drawn to reflect the change in their parent, as explained below.

As explained above, the closest point is typically considered the closest point along the base-curve 104b of vascular objects neighboring the dropped element as the element is moved about the stage 50 before being dropped thereon. After dropping the element and identifying the closest base-curve point, the element may then snap to a point along one of the sides 104a of the respective object, the snap-to point typically having the same percent value as the closest point along the respective base-curve. Thus, the snap-to point may be utilized to further refine the positioning of the dropped element and inform the shape the dropped element may take. As used herein, references may be made to the "snap-to point." It should be understood, however, that the snap-to point may be the closest point along the base-curve or along one of the sides. Alternatively, the snap-to point may refer to a point along the side that corresponds (e.g., has the same percent value along the parent object) to the closest point along the base-curve, as explained above.

A snap-to point can be considered anatomically feasible based upon a number of different factors including, for example, one or more predefined characteristic restrictions imposed by the dropped element. For example, a branch 70 may be restricted to only snap to another branch such that, when a branch is dropped onto the stage, its control point A snaps to the closest point of another branch. Also, for example, a graft 92 may be restricted such that the graft's control point A snaps to a point along another graft only if it is directly dropped on the respective snap-to point of the other graft; otherwise, the graft's control point A snaps to the closest of several predetermined points within the aorta 52. Control point B of the graft, then, may be restricted to only snap to the closest point of a branch, for example. With respect to collaterals, for example, both control points A and B may be restricted to only snap to a branch, or a pair of branches. Further, as an ostial stenosis occurs at the ostium (i.e., origin) of a branch or graft, an ostial stenosis may be restricted such that its control point A only snaps to the closest origin point of a branch or graft.

To facilitate generating a text-based report from the diagram built on the stage 50 of the GUI, each element type (branches 70, collaterals 74, stenosis 80, irregularities 86, ectasia 90, grafts 92, stents 96, thrombus 79, ulcerated plaques 83, calcification 87, etc.) can be assigned to a respective holder array (e.g., branch holder array, graft holder array, etc.) as or after the respective element is dropped onto the stage and snapped to an object (or the aorta 54), as shown in block 26. In this regard, upon loading the base representation 52, the holder arrays typically begin empty, and are then populated as elements of the respective types are dropped onto the stage, and thus added to the diagram. Typically, the holder arrays are lists internal to the visual reporting application 8 that allow the application to dynamically and thoroughly maintain and control the elements on the diagram. In this regard, when an element is dropped onto the stage, the element can be assigned an associated, unique holder-reference name or other identifier, such as based upon the number of other similar type elements already on the stage. For example, the third graft dropped onto the stage, and thus added to the diagram, may be assigned a holder-reference name ending with the identifier "graft_3." The holder-reference name for an element can then be linked to the respective element's attributes and passed into the appropriate holder array such that, when the holder-reference name is called upon, the attributes of the respective element can be retrieved. The holder-reference name is typically absolute in that it only ever refers to the one element and never changes as long as the respective element remains on the stage, irrespective of whether the respective element is moved or otherwise manipulated.

Because the holder arrays are object-specific, the arrays can reduce computation time otherwise required of the visual reporting application 8 in that functions and queries relevant to only a certain element type can be directed to the desired holder array instead of filing through every element on the stage. A holder array can be queried to populate separate, temporary arrays, containing elements matching a given criteria where the elements can be re-sorted into a different order. For example, a temporary array can be created to sort lateral branches 70 in their consecutive order down the left side 104a of the left coronary artery 56, thus identifying the ordination attribute of the lateral branches. In this regard, the temporary array typically begins empty when the branch holder array is queried. The attributes of each branch relevant to the query (e.g., branches that are connected or otherwise snapped to the left side of the left coronary artery) can be located via the holder-reference names. The temporary array can then be populated by references (i.e., holder-reference names) to those branches found to satisfy the query. As or after the temporary array is populated, the references can be resorted within the temporary array in ascending numerical order of the referenced branches' snap-to points along the left side of the left coronary artery, for example.

Consider, for example, a user dropping a branch 70 (branch_1) onto the stage 50 and snapping that branch to the left side 104*a* of the left coronary artery 56 at snap-to point 40, dropping another branch (branch_2) to the same side at snap-to point 24, and then dropping yet another branch (branch_3) to the same side at snap-to point 52. In such an instance, the holder-reference names for these branches can be passed into the branch holder array by their order of addition. Likewise, to determine the branch ordination attribute for the dropped branches, a secondary, temporary array can be created and populated by re-sorting these reference names by their snap-to point, so that branch_2, branch_1 and branch_3 have associated ordination attributes of first, second and third, respectively.

Also as an object is snapped to a parent, angle attributes of the object can be identified or otherwise determined, such as to identify a side of the parent to which the object snaps, and thus extends, as shown in block 28. As shown in FIGS. 8*a*-8*c*, for example, consider a reference point 106 along the base-curve 104*b* of the parent object corresponding to the object's snap-to point at the parent. From the reference point, an assumed, vertical reference line 108 is established to intersect the reference point, where an angle may be measured clockwise from the reference line beginning at zero degrees. In addition to the reference line, consider an assumed tangent line 110 from the base-curve of the parent object at the reference point. Also, consider an assumed curve point at an intersection of tangents from the origin and termination points along the base-curve of the child object, and an associated curve line 112 formed between the curve point and reference point. With the vertical line, tangent line and curve line, a snap-to angle 114 and a curve angle 116 can be identified. As shown, for example, the snap-to angle can be identified as the angle from the vertical line to the tangent line, while the curve angle can be identified as the angle from the tangent line to the curve line.

After identifying the snap-to angle 114 and curve angle 116, the side 104*a* of the parent to which the object is snapped, and therefore from which the object extends, can be identified such that the object is snapped to the identified side. For example, if the child's curve angle is between the snap-to angle and the difference between the snap-to angle and 180 degrees, the child is typically snapped to a snap-to point along the right side of its parent object; otherwise the child object is snapped to a snap-to point along the left side of its parent object. Typically, the side of the tangent line 110 where the curve point is located is also the side of the parent object to which the child object snaps. Even in such an instance, however, it should be understood that, because the curve angle does not depend on the location of the child's termination point, the child can be made to cross over its parent without switching the side of the parent to which it is attached, as shown in FIG. 8*c*.

After an element snaps to a point at a parent object, the position (e.g., snap-to point), length (e.g., number of points along the element's length), and parent (i.e., parent object) attributes can be accordingly identified or otherwise determined. Similarly, the angle attributes of the element can be determined, as explained above. Further, the element's name can be identified based upon the element type. Alternatively, as the name of one or more elements may differ depending upon the element's direction, the visual reporting application 8 can dynamically determine the name of one or more elements based upon geometrical analysis of the element's direction and one or more anatomical rules, where the element's direction may be defined by the element's position, length and angle attributes.

As shown in FIGS. 9*a*-9*c*, consider a branch 70 dropped onto the stage 50 and snapped to the circumflex 60 such that the branch extends from the left side 104*a* of the circumflex. In such an instance, the dropped branch can have one of three names depending on the branch's position and, in various instances, its direction of flow. As shown in FIG. 9*a*, if the dropped branch snaps to a point associated with a percent value less than 3% of the circumflex's length (regardless of direction of flow), the dropped branch is said to trifurcate and is named "ramus intermedius" 70*a*. If, however, the dropped branch snaps to a point associated with a percent value equal to or greater than 3% of the circumflex's length and courses in an approximately perpendicular direction (e.g., extending approximately 90° or 270°—plus or minus up to 45°—off the circumflex), the dropped branch is named "obtuse marginal" 70*b*, as shown in FIG. 9*b*. Lastly, if the dropped branch snaps to a point with a percent value greater than 66% of the circumflex's length (within the distal third) and courses in a downward direction (e.g., extending approximately 180°— plus or minus up to 45°—off the circumflex), the dropped branch represents a branch supplying blood to the heart's posterior and is accordingly named the "left posterior descending artery" 70*c*, as shown in FIG. 9*c* (as opposed to the right posterior descending artery, which arises from the right coronary artery 58).

For each element that is dropped onto the stage 50 or loaded with the base representation 52, the element can, but need not, be moved and/or shaped on the stage, with the visual reporting application 8 identifying or otherwise determining a number of parameters associated with the dropped element, as shown in block 30. Also, at any point after loading the elements of the base representations or dropping an element onto the stage, one or more elements may be moved at one or more instances to any other feasible snap-to point on the same or a different object. Additionally or alternatively, the shape and/or one or more attributes of one or more elements may be manipulated at one or more instances. More particularly as to modifiers, the length of such elements may be changed via a drag point 118 at the end of the modifier that allows the user to stretch the shape along the length of its parent vascular object, as shown in FIG. 10 with respect to an irregularity 86 snapped to the circumflex 60.

Figure 11A:
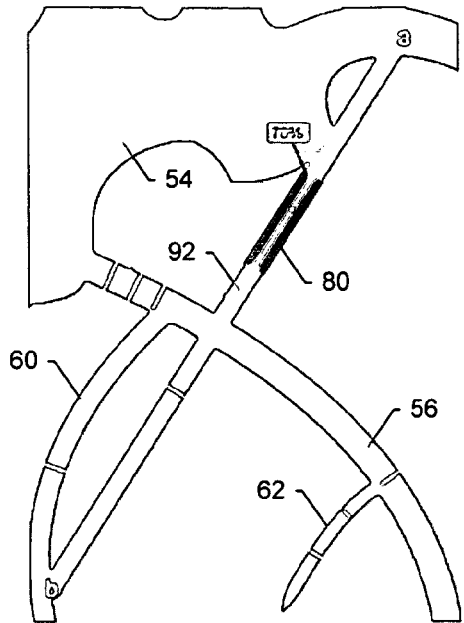
Figure 11B:
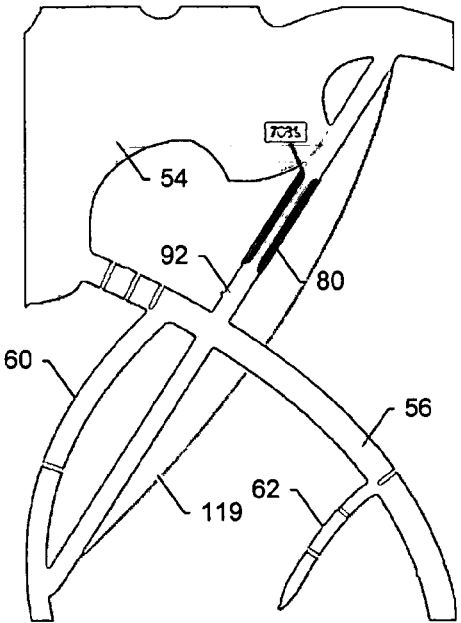
Figure 11C:
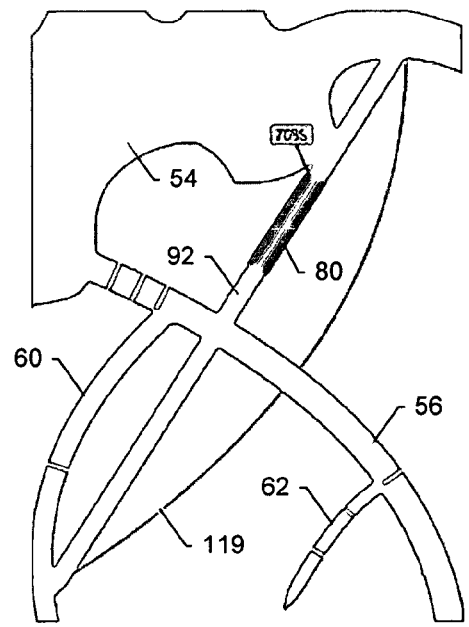
Figure 11D:
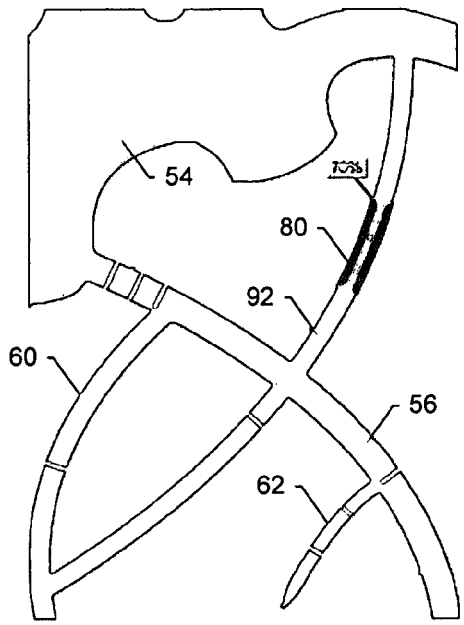

More particularly, for example, consider a graft 92 having a control point A snapped to the aorta 54 and a control point B snapped to the circumflex 60, where the graft has a stenosis 80 (70%) snapped thereto, as shown in FIG. 11*a*. After snapping the graft to the aorta and circumflex, the graft may be reshaped by adjusting the curvature such as to bend the graft further away from the aorta. In such an instance, the graft may be reshaped by selecting the graft and reshaping the graft to the desired curvature. For example, the graft may be reshaped by positioning a user interface pointer over the graft and actuating a button of the mouse 11 to select the graft. With the button actuated, the pointer is then moved to the desired position of the graft, after which the button is released to set the desired position, and thus curvature, of the graft. As the pointer is moved over a number of positions from the original position to the desired position, the visual reporting application 8 may present a preview line 119 to illustrate the position and thus the curvature of the graft at each position should those positions be selected as the desired position, as shown in FIG. 11b. When such a preview line is presented, the preview line moves with the pointer to the desired position, as shown in FIG. 11c. After setting the desired position, the graft is redrawn to assume the shape of the preview line, and the preview line is removed or otherwise disappears, as shown in FIG. 11d.

As will be appreciated, one or more attributes associated with any element on the stage 50 may change when that element is moved or re-shaped, or via a right-click menu. More particularly with respect to such a right-click menu, a user may select an element by positioning the user interface pointer over the element and actuating a button, such as a right button, of the mouse 11. Upon actuating the button, the visual reporting application 8 presents a menu specific to the selected element, from which a user may select a new value for one or more attributes of the respective element. Then, after selecting a new value for one or more attributes (if new values are selected), the selected element and any dependant elements may be immediately re-drawn to reflect the change in attribute value.

As will also be appreciated, when a parent object is moved or re-shaped, its children may be accordingly assigned new snap-to points whose associated percent value corresponds to the percent value associated with the respective child's previous snap-to point. As a result, children are typically positioned relative to their parent's length, and are typically not orphaned if the parent is considerably shrunk. For example, a modifier originating at the 80% point of its parent object (i.e., within the distal third) will remain at the 80% point even if the parent is stretched, shrunk, curved, or repositioned, even in a manner that changes the absolute snap-to point. Thus, although the child's snap-to point number may change, the associated percent value of the snap-to point typically remains constant (unless the child is separately moved).

As elements are dropped onto the stage 50 and/or moved and/or shaped on the stage, one or more elements may overlap. In this regard, the visual reporting application 8 is capable of automatically determining what elements should or should not overlap, or otherwise stacking elements (e.g., setting the z-axis depth) on the stage based upon the respective element's type, position and/or neighboring elements. For example, branches 70, grafts 92 and collaterals 74 can each be assigned a unique depth zone in ascending order such that collaterals appear above grafts, and grafts appear above branches. A number of depth-setting rules also place dependent modifiers (stents 96, stenosis 80, irregularities 86, ectasia 90, thrombus 79, ulcerated plaques 83, calcification 87, etc.) at a depth relative to their respective parent object (e.g., branch or graft). For example, when dropped onto the stage, irregularities and ectasia modifiers can be set as low as possible above their parent object, with any overlapping stents set above irregularities and ectasia, any overlapping stenosis above stents. Further, for example, any overlapping thrombus can be set above stenosis, with any overlapping ulcerated plaques set above thrombus, and any overlapping calcification set above ulcerated plaques. Advantageously, the visual reporting application is capable of setting the depth of elements as those elements or their parent objects are drawn or re-drawn, thereby dynamically maintaining accuracy of the diagram through any manipulation.

As shown in block 32, a number of elements, including vascular objects and dependent modifiers, can be selected and dropped onto the stage 50. As suggested above, for each element dropped onto the stage, the element can snap to an object of the diagram, with associated parameters identified/determined. Further, the element can, if so desired, be moved and/or shaped at one or more instances after snapping the element to an object, as shown in blocks 34 and 30.

Upon completing or otherwise saving a diagram presented on the stage 50, the holder arrays and the attributes of the objects the holder arrays reference can be compiled into a list, such as a list formatted in accordance with the Extensible Markup language (XML). Thus, upon loading a previously completed or otherwise saved diagram, the holder arrays may be repopulated from the list, with the completed/saved diagram recreating each object referenced in each holder array with its respective appropriate attributes. In this regard, since the holder-reference names within holder arrays can be ordered by the succession in which the respective objects were added to the diagram, a re-loaded diagram can populate the stage in the same order that the user added those objects to the diagram. This ensures that dependent objects are not lost or orphaned, as their parents are loaded prior to the respective dependent objects.

B. Generating a Text-Based Report from the Graphical Illustration/Diagram

As explained above, the visual reporting application 8 is capable of dynamically determining the anatomically correct names and other attributes associated with each element on the stage 50 of the GUI through user manipulation and geometric analysis. The application is adapted to understand any change in the diagram at the moment the change occurs, and can readily generate a text-based report from the diagram at any time, awaiting only the user's satisfaction with the diagram, as shown in block 36. Thus, the user is not restricted to performing tasks in a given order, and can adopt any workflow without detriment to the accuracy of the final text-based report. As explained below, the visual reporting application is capable of automatically generating a text-based report by ordering each object's name and attributes by their nested structure into physiologically and grammatically accurate sentences.

The report generated by the visual reporting application 8 is designed to mimic and replace a natural language report that the user, such as a cardiologist, would otherwise create from viewing a diagram such as one generated in the application. In the context of reporting a cardiac catheterization procedure, every element illustrated in the diagram can be reported along with its significant attributes, and ordered by the methods standard to cardiological reporting—hierarchy, dependency, location/origin, and direction of flow. In any instance, however, the application is advantageously capable of dynamically and automatically generating the text-based report without or otherwise independent of user input after creating the diagram, the report being generated therefrom.

As explained above, the attributes of each object of the diagram can be identified or otherwise determined when that object is dropped onto the stage 50 and snapped to another object of the diagram. In addition, every object has a holder-reference name representing that object in a respective holder array, where the holder-reference name links to the respective object's attributes. Thus, when a user has created a diagram and directed the visual reporting application 8 to create a text-based report therefrom, the drawing phase ends. Thereafter, the visual reporting application examines each element in each holder array by following a nested hierarchy of parent-child-grandchild relationships, and assigns language strings based upon the examination. As shown in the control or examination flow diagram of FIG. 12, for example, the major vessels at the top of the hierarchy are examined in the order: the left coronary artery 56 (formed by the left main, if present, and the left anterior descending), the circumflex 60, and the right coronary artery 58. Each branch 70 is first examined for its own attributes, followed by any objects dependent on the branch and the attributes of those dependent objects.

The nested hierarchy for branches 70 and their children elements is ordered as follows. The branch itself is examined and language strings are assigned for its attributes (see FIG. 12, 120). The holder arrays for each modifier type are then examined to identify modifiers dependent on the branch (e.g., based upon the parent attribute), after which the dependent modifiers can be examined and language strings assigned for their attributes (see 122). As shown, for example, the modifier holder arrays can be examined in the following order: stent holder array, stenosis holder array, irregularities holder array, ectasia holder array, thrombus holder array, ulcerated plaques holder array and calcification holder array. During examination of each modifier, the visual reporting application can determine which segment or segments of the parent branch within which the modifier is located (e.g., based upon the position attribute and/or the length attribute). Accordingly, the visual reporting application 8 can assign an appropriate language string based upon the percent values of the points along the branch occupied by the modifier. For example, a tubular stenosis that stretches from the points between 50% and 70% the length of the right coronary artery 58 may be qualified as being within its "mid and distal segments." Within this nesting, the separate modifiers can be ordered by their location along the parent branch, beginning with the modifier closest to its origin point. For example, stents may be listed by the ascending value of their snap-to points, with stenosi thereafter listed in a likewise manner, and so forth.

In addition to examining each modifier holder array, the collaterals holder array can be examined to determine if any collaterals 74 are snapped to the branch 70. For any such collaterals, the branch(es) and segment(s) of those branch(es) to which the collaterals are snapped can be determined, with appropriate language strings thereafter being assigned to the collaterals and their attributes (see 124). Similar to modifiers, collaterals can likewise be ordered by their location.

Further, the branch holder array can be examined to determine any lateral branches 70 that depend on the branch (the respective branch being a parent to the child lateral branches dependent thereon). If so, each dependent lateral branch can be examined and language strings assigned for their attributes (see 126). Additionally, the branch holder can be examined to determine if any children lateral branches themselves have any children modifiers or branches. If so, the children elements can be examined, such as in the following order: modifiers and their attributes in their respective holders, collaterals and their attributes, and then lateral branches and their attributes (see 128-136). During such examinations, the collection of information about each branch and its dependents can be ordered by the branch's position and ordination attribute.

In addition to examining and assigning language strings for branches 70 and their dependents, a similar process can be conducted for grafts 92. For example, grafts and their modifiers can be similarly examined and assigned language strings in an order based upon the branches to which the grafts are connected. More particularly, for example, the general order, determined by an examination of the members of the graft holder array, can begin with grafts snapped to the left main portion of the left coronary artery 56 (should it exist) in ascending order of the value of their control point B snap-to points, followed by any lateral branches dependent on the left main by ascending snap-to point values of the respective lateral branches. Then, the order of examining grafts can proceed to those snapped to the left anterior descending portion of the left coronary artery, such as in the same manner as those snapped to the left main portion. Next, grafts snapped to the circumflex 60 can be examined in ascending order of the value of their control point B snap-to points, followed by any grafts snapped to any lateral branches that, in turn, are snapped to the circumflex by ascending snap-to values of the lateral branches. Finally, grafts snapped to the right coronary artery 58 can be examined, such as in the same manner as those snapped to the circumflex and dependents of the circumflex.

As each graft 92 within the graft holder array is examined, a language string is assigned to the graft based upon its attributes. Also, the percent value of the graft's control point B snap-to point along the side 104a of its parent branch 70 can be identified or otherwise determined, thereby determining the segment of the parent branch to which the graft is snapped such that the assigned language string can be based upon the respective segment. The modifier holder arrays can also be examined to identify modifiers dependent on the graft, after which the dependent modifiers can be examined and language strings assigned for their attributes, such as in the same manner as modifiers dependent on branches.

As indicated above, when generating a text-based report, the visual reporting application 8 can assign a language string to each element and attribute. In this regard, each assigned language string can include one or more words, phrases, clauses or the like. To generate a report, then, the assigned language strings can be compiled into sentences, which can be dynamically corrected by functions that ensure grammatical accuracy, such as by checking punctuation, plurality, spacing, appropriate article, capitalization and the like. Advantageously, the visual reporting application may also alternate between a number of alternate strings or portions thereof (e.g., phrases) having similar meaning to further mimic natural language. For example, the visual reporting application may randomly choose between the phrases "which arises from the" and "arising from the" when describing the aortic cusp from which a branch 70 originates.

The method employed by the visual reporting application 8 to achieve a natural language report typically includes placing supporting words, phrases, clauses or the like (text strings) proximate the attributes (e.g., character-based, numerical, etc.) of the diagram's elements to thereby derive sentences that can then be ordered and concatenated into full, grammatically correct sentences. For example, a language string describing the caliber of a given branch 70 can be derived by calling the caliber attribute (e.g., small, medium, large) via the branch's holder-reference name in the branch holder. This attribute value can then be set inside a supporting phrase in which a grammatical space has been reserved for it. For example, the caliber of a given branch can be set inside the supporting phrase "is a _____ caliber branch" such that, when the caliber value is "medium," the assigned language string comprises "is a medium caliber branch."

The visual reporting application 8 may also create and assign a language string describing the segment of a branch 70 upon which a dependent object is snapped by examining the position and length attributes of that dependent object. In the case of modifiers, the visual reporting application can determine which segment or segments of the branch upon which the modifier is located by calculating the percentages of the points along the branch framing the modifier. For example, if a tubular stenosis stretches from points having associated percent values between 50% and 70% along the length of the right coronary artery 58, a language string such as "mid and distal segment" can be assigned to the modifier to thereby describe the respective segments across which the tubular stenosis extends. For vascular objects, on the other hand, a language string describing the segment to which the object is snapped may be derived only from the percent value associated with the single snap-to point on its parent object. Thus, a language string such as "proximal segment", "mid segment" or "distal segment" may be assigned to a dependent object; as opposed to a language string including a combination of segments as may be the case with a modifier.

The visual reporting application 8 can further implement an indefinite article function to appropriately supply either "a" or "an" before a word or number in the text-based report. Generally, the article function examines whether the first letter of a word is a vowel or if the first digit of a number is 8 (the only digit which is pronounced with a beginning vowel sound). If so, the article "an" is set before that word or number in the language string; otherwise, the article "a" is set before that word or number. Also when constructing language strings, object attributes with values that denote a plurality are recognized, and the appropriate linking verbs are chosen. For example, when describing a plurality of dependent collaterals, the language string may be formed to read "there are faint collaterals . . . ." Similarly, when describing the degree of a concentric stenosis, the language string may be formed to read "there is an 85% concentric stenosis . . . ." Moreover, irrespective of how the language strings are generated and assigned to elements and their attributes, once the application has concatenated the language strings into a sentence or sentences, the application can capitalize the first letter of the first word of each sentence and place punctuation appropriate to the sentence(s) to thereby complete grammatically accurate sentences.

Once generated, the visual reporting application 8 can present the report on the display 10 for viewing by the user. The report can be presented in any of a number of different manners including, for example, within an editable text area of a modal window 120, such as a modal window that preempts user interaction in all other parts of the application while open, as shown in FIG. 14 for the diagram created on the stage 50 of FIG. 13. The user is thereby permitted the opportunity to review and optionally edit the generated report, such as by making any desired additions, remissions and/or changes to the report. If so desired, the user can also direct the visual reporting application to send the generated report to a word processor or other application capable of being operated by the computer 6. In such instances, the generated report can be sent in any of a number of different formats including, for example, a rich text format (RTF), as shown in FIG. 15. Advantageously, as explained above, the visual reporting application is capable of dynamically and automatically generating the report shown in FIGS. 14 and 15 solely based upon the graphical diagram of FIG. 13 (and shown in the background of FIG. 14) created by the user adding, deleting and/or manipulating one or more elements on the stage 50 of the application GUI.

In addition, the visual reporting application 8 can save the report to memory, along with or separate from the corresponding diagram. For example, the application can connect to a database, such as a SQL (Structured Query Language) or a Microsoft Access database, local to or remote from the computer 6 (e.g., within memory device 4). In this regard, in addition to saving the report to memory, the application may be configured to transfer the report/diagram to a remote location, such as a medical facility, where the report/diagram can be saved in memory. Thus, in the context of reporting a cardiac catheterization procedure of a patient, the report/diagram can be saved along with other information regarding the patient.

As described throughout, a number of steps and/or substeps in the method of embodiments of the present invention are shown and described as being performed in a particular order. Likewise, a number of elements are shown and described as having an ordered relationship with respect to one another. It should be understood, however, that the illustrated and described ordering of steps and elements are merely illustrative, and should therefore not be taken to limit the scope of the present invention. Thus, in various instances, one or more of the steps may be performed in an order different from that described above. Additionally or alternatively, in various instances, one or more elements may have an ordered relationship different from that described above.

It should also be understood that in lieu of receiving one or more attributes of one or more elements from a user, the visual reporting application 8 may import one or more attributes from one or more other sources, if so desired. For example, one or more attributes may be imported from a patient record database storing such attribute(s). Additionally or alternatively, one or more attributes may be imported from one or more systems capable of measuring such attribute(s). Further, in one or more instances the report generated from the diagram may be, in turn, incorporated into a more detailed report including additional information that the application may not be capable of garnering from the diagram alone. For example, in addition to anatomical findings and/or summary that may be included in the report generated from the diagram, a cardiac catheterization report may also include other pieces of information such as the physician's name, patient demographics, procedure notes, hemodynamic readings or the like that may also be incorporated into a more detailed report. Also in such instances, the report generated from the diagram, along with one or more pieces of additional information, may be imported into the more detailed, final report. In this regard, in cases of cardiac catheterization reports, many, if not most, of the additional information may be already available via a hemodynamic monitoring system. Thus, in the interest of reducing or eliminating the need for user entry, the application can be configured to import additional information from the hemodynamic system and automatically add it to the final report.

In addition, although embodiments of the present invention are shown and described as generating a report from the diagram, it should be understood that the visual reporting application 8 may be configured to generate a report from the entire diagram, or one or more selected portions of the diagram. In this regard, the visual reporting application may be configured to receive one or more selections of one or more elements of the diagram, and thereafter generate a report from the selection(s) of element(s). Additionally or alternatively, the visual reporting application may be configured to generate a report with more abbreviated language strings being assigned to the elements. In such instances, instead of mimicking a complete natural language report, the report mimics a summary report. To generate the summary report, then, the visual reporting application may or may not assign the more complete language strings to elements and attributes, but instead assign abbreviated language strings from which less-than-full sentences, or just phrases, may be formed and concatenated.

Further, as shown and described herein, an entity is graphically illustrated with a report generated from the illustration. It should be understood, however, that the visual reporting application 8 may be alternatively configured to facilitate generating a text-based report regarding an entity based, at least in part, on user input, and thereafter automatically and dynamically generate a graphical illustration of the entity from the report. In such instances, the visual reporting application may employ a semantic neural network. As is known to those skilled in the art, neural networks are modeled upon the human brain's interconnected system of neurons. Based upon this premise, the neural network allows the application to imitate the brain's ability to sort out patterns and learn from trial and error, discerning and extracting the relationships that underlie input text strings to thereby illustrate graphical illustrations of elements related to those text strings.

According to one aspect of the present invention, the system (computer 6) of the present invention generally operates under control of a computer program product, referred to in various embodiments as the visual reporting application 8. The computer program product for performing the methods of embodiments of the present invention includes a computer-readable storage medium, such as the non-volatile storage medium, and computer-readable program code portions, such as a series of computer instructions, embodied in the computer-readable storage medium.

In this regard, FIG. 2 is a flowchart of methods, systems and program products according to the invention. It will be understood that each block or step of the flowchart, and combinations of blocks in the flowchart, can be implemented by computer program instructions. These computer program instructions may be loaded onto a computer (e.g., computer 6 on FIG. 1) or other programmable apparatus to produce a machine, such that the instructions which execute on the computer or other programmable apparatus create means for implementing the functions specified in the flowchart block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the flowchart block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the flowchart block(s) or step(s).

Accordingly, blocks or steps of the flowchart support combinations of means for performing the specified functions, combinations of steps for performing the specified functions and program instruction means for performing the specified functions. It will also be understood that each block or step of the flowchart, and combinations of blocks or steps in the flowchart, can be implemented by special purpose hardware-based computer systems which perform the specified functions or steps, or combinations of special purpose hardware and computer instructions.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus comprising:
a local or remote memory device storing executable instructions; and
a processor configured to interact with and execute the instructions in the memory device, wherein execution of the instructions causes the processor to at least perform the following operations:
providing a diagram of a vascular system having at least one vascular object associated with a plurality of attributes, the at least one vascular object including a first vascular object having a length along which a finite number of greater than two interpretable points are positioned with a constant spacing therebetween, wherein each point is assigned a value representing a percent of the length of the respective vascular object along which the point is positioned;
receiving user input to build the diagram of the vascular system, wherein receiving user input to build the diagram includes:
 receiving user input to add at least one additional vascular object or modifier to the diagram, the at least one additional vascular object or modifier including at least one second vascular object or modifier, and based on the receiving, snapping the second vascular object or modifier to one of the number of points on the first vascular object, the respective one of the number of points constituting a snap-to point; and thereafter,
 receiving user input to manipulate the shape of the first vascular object, and based on the receiving, increasing or decreasing the length of the first vascular object such that the number of points along the length of the first vascular object increases or decreases to thereby maintain the constant spacing, and such that the value assigned to the snap-to point is reassigned to another point on the first vascular object to reflect a change in percent of the length of the first vascular object along which the snap-to point and other point are positioned;
reassigning the second vascular object or modifier from the snap-to point to the other point such that the respective other point thereafter constitutes the snap-to point;
determining a plurality of attributes associated with each vascular object added to the diagram; and
automatically generating a text-based report from the diagram without user input other than the user input received to build the diagram, wherein the generating operation includes:
 examining each vascular object by following a nested hierarchical ordering;
 assigning at least one language string for each vascular object and associated attribute based upon the examination, each language string constituting a component of a sentence; and
 compiling the language strings into sentences, and ordering and concatenating the sentences into the text-based report, including compiling each of one or more pluralities of language strings into a single sentence.

2. An apparatus according to claim 1, wherein the receiving user input to add at least one additional vascular object or modifier operation comprises:
receiving user input to select a second vascular object or a modifier from a menu;

receiving user input to drag the selected second vascular object or modifier from the menu to a stage including the diagram;

receiving user input to drop the selected second vascular object or modifier onto the stage; and snapping the selected second vascular object or modifier to one of the number of points on the first vascular object.

3. An apparatus according to claim 2, wherein the snapping operation comprises:

determining a snap-to point from the number of points on the first vascular object based upon at least one predefined characteristic restriction imposed by the selected second vascular object or modifier; and snapping the selected second vascular object or modifier to the determined snap-to point.

4. An apparatus according to claim 2, wherein the receiving user input to add operation includes receiving user input to add a modifier, including:

snapping the modifier to the first vascular object from which the modifier depends, the number of points on the first vascular object including a finite plurality of interpretable points along a length of, and proximate each of a pair of sides of, the vascular object;

framing a shape of the modifier by a series of consecutive points on the vascular object; and fitting a stock representation of the modifier to the series of consecutive points framing the shape of the modifier to thereby form-fit the modifier to the vascular object.

5. An apparatus according to claim 1, wherein the receiving user input to manipulate operation further comprises receiving user input to increase or decrease a curvature of the vascular object.

6. An apparatus according to claim 1, wherein the receiving user input to add operation includes receiving user input to add a second vascular object, the selected second vascular object comprising a child vascular object and the first vascular object comprising a parent vascular object, the parent vascular object including a pair of sides, and wherein the snapping operation comprises:

determining an angle attribute of the child vascular object;

determining a side of the parent vascular object to which the child vascular object snaps; and snapping the child vascular object proximate to the determined side of the parent such that the child vascular object extends from the determined side.

7. An apparatus according to claim 1, wherein the determining operation comprises for at least one vascular object added to the diagram of the vascular system:

determining a position attribute, a length attribute and an angle attribute associated with the vascular object, the position, length and angle attributes defining a direction of the vascular object; and determining a name attribute associated with the vascular object based upon the direction of the vascular object and at least one rule.

8. An apparatus according to claim 1, wherein the vascular objects of the diagram comprise vascular objects of a plurality of vascular object types, and wherein the execution of the instructions causes the processor to further perform the following operations:

assigning each vascular object of the diagram to a respective holder array, each holder array including an identifier for each vascular object assigned to the holder array, the identifier being linked to the attributes associated with a respective vascular object, wherein the generating operation comprises generating a text-based report based upon the holder arrays and the attributes linked to the vascular object identifiers in the holder arrays.

9. An apparatus according to claim 1, wherein the assigning operation includes placing at least one supporting word at least one of before or after an attribute to thereby assign a language string to the attribute.

10. An apparatus according to claim 1, wherein the compiling operation includes compiling the language strings into sentences based upon at least one function to correct any grammatical errors and thereby increase grammatical accuracy of the sentences.

11. An apparatus according to claim 1, wherein the providing operation comprises providing a diagram of a heart, the diagram including vascular objects comprising at least one vascular object representing at least one of a branch, a graft or a collateral, and at least one modifier depending from at least one vascular object, the at least one modifier representing at least one of a stent or an aberration.

12. A method comprising:

performing, by an apparatus including a processor configured to interact with a local or remote non-transitory memory device storing executable instructions, a number of steps including at least the following steps:

providing, by the processor, a diagram of a vascular system having at least one vascular object associated with a plurality of attributes, the at least one vascular object including a first vascular object having a length along which a finite number of greater than two interpretable points are positioned with a constant spacing therebetween, wherein each point is assigned a value representing a percent of the length of the respective vascular object along which the point is positioned;

receiving user input to build the diagram of the vascular system, wherein receiving user input to build the diagram includes:

receiving user input to add at least one additional vascular object or modifier to the diagram, the at least one additional vascular object or modifier including at least one second vascular object or modifier, and based on the receiving, snapping the second vascular object or modifier to one of the number of points on the first vascular object, the respective one of the number of points constituting a snap-to point; and thereafter, receiving user input to manipulate the shape of the first vascular object, and based on the receiving, increasing or decreasing the length of the first vascular object such that the number of points along the length of the first vascular object increases or decreases to thereby maintain the constant spacing, and such that the value assigned to the snap-to point is reassigned to another point on the first vascular object to reflect a change in percent of the length of the first vascular object along which the snap-to point and other point are positioned;

reassigning the second vascular object or modifier from the snap-to point to the other point such that the respective other point thereafter constitutes the snap-to point;

determining a plurality of attributes associated with each vascular object added to the diagram; and automatically generating a text-based report from the diagram without user input other than the user input received to build the diagram, wherein the generating step includes:

examining each vascular object by following a nested hierarchical ordering;

assigning at least one language string for each vascular object and associated attribute based upon the examination, each language string constituting a component of a sentence; and compiling the language strings into sentences, ordering and concatenating the sentences into the text-based report, including compiling each of one or more pluralities of language strings into a single sentence.

13. A method according to claim 12, wherein the receiving user input to add at least one additional vascular object or modifier step comprises:

receiving user input to select a second vascular object or a modifier from a menu;

receiving user input to drag the selected second vascular object or modifier from the menu to a stage including the diagram;

receiving user input to drop the selected second vascular object or modifier onto the stage; and snapping the selected second vascular object or modifier to one of the number of points on the first vascular object.

14. A method according to claim 13, wherein the snapping step comprises:

determining a snap-to point from the number of points on the first vascular object based upon at least one predefined characteristic restriction imposed by the selected second vascular object or modifier; and snapping the selected second vascular object or modifier to the determined snap-to point.

15. A method according to claim 13, wherein the receiving user input to add step includes receiving user input to add a modifier, including:

snapping the modifier to the first vascular object from which the modifier depends, the number of points on the first vascular object including a finite plurality of interpretable points along a length of, and proximate each of a pair of sides of, the vascular object;

framing a shape of the modifier by a series of consecutive points on the vascular object; and fitting a stock visual representation of the modifier to the series of consecutive points framing the shape of the modifier to thereby form-fit the modifier to the vascular object.

16. A method according to claim 12, wherein the receiving user input to manipulate step further comprises receiving user input to increase or decrease a curvature of the vascular object.

17. A method according to claim 12, wherein the receiving user input to add step includes receiving user input to add a second vascular object, the selected second vascular object comprising a child vascular object and the first vascular object comprising a parent vascular object, the parent vascular object including a pair of sides, and wherein the snapping step comprises:

determining an angle attribute of the child vascular object;

determining a side of the parent vascular object to which the child vascular object snaps; and snapping the child vascular object proximate to the determined side of the parent such that the child vascular object extends from the determined side.

18. A method according to claim 12, wherein the determining step comprises for at least one vascular object added to the diagram of the vascular system:

determining a position attribute, a length attribute and an angle attribute associated with the vascular object, the position, length and angle attributes defining a direction of the vascular object; and determining a name attribute associated with the vascular object based upon the direction of the vascular object and at least one rule.

19. A method according to claim 12, wherein the vascular objects of the diagram comprise vascular objects of a plurality of vascular object types, and wherein performing a number of steps further includes at least the following steps:

assigning each vascular object of the diagram to a respective holder array, each holder array including an identifier for each vascular object assigned to the holder array, the identifier being linked to the attributes associated with a respective vascular object, wherein the generating step comprises generating a text-based report based upon the holder arrays and the attributes linked to the vascular object identifiers in the holder arrays.

20. A method according to claim 12, wherein the assigning step includes placing at least one supporting word at least one of before or after an attribute to thereby assign a language string to the attribute.

21. A method according to claim 12, wherein the compiling step includes compiling the language strings into sentences based upon at least one function to correct any grammatical errors and thereby increase grammatical accuracy of the sentences.

22. A method according to claim 12, wherein the providing step comprises providing a diagram of a heart, the diagram including vascular objects comprising at least one vascular object representing at least one of a branch, a graft or a collateral, and at least one modifier depending from at least one vascular object, the at least one modifier representing at least one of a stent or an aberration.

23. A non-transitory computer-readable storage medium having computer-readable program code portions stored therein that in response to execution by a processor cause the processor to at least perform the following operations:

providing a diagram of a vascular system having at least one vascular object associated with a plurality of attributes, the at least one vascular object including a first vascular object having a length along which a finite number of greater than two interpretable points are positioned with a constant spacing therebetween, wherein each point is assigned a value representing a percent of the length of the respective vascular object along which the point is positioned;

receiving user input to build the diagram of the vascular system, wherein receiving user input to build the diagram includes:

receiving user input to add at least one additional vascular object or modifier to the diagram, the at least one additional vascular object or modifier including at least one second vascular object or modifier, and based on the receiving, snapping the second vascular object or modifier to one of the number of points on the first vascular object, the respective one of the number of points constituting a snap-to point; and thereafter, receiving user input to manipulate the shape of the first vascular object, and based on the receiving, increasing or decreasing the length of the first vascular object such that the number of points along the length of the first vascular object increases or decreases to thereby maintain the constant spacing, and such that the value assigned to the snap-to point is reassigned to another point on the first vascular object to reflect a change in percent of the length of the first vascular object along which the snap-to point and other point are positioned;

reassigning the second vascular object or modifier from the snap-to point to the other point such that the respective other point thereafter constitutes the snap-to point;

determining a plurality of attributes associated with each vascular object added to the diagram; and automatically generating a text-based report from the diagram without user input other than the user input received to build the diagram, wherein the generating operation includes:
examining each vascular object by following a nested hierarchical ordering;
assigning at least one language string for each vascular object and associated attribute based upon the examination, each language string constituting a component of a sentence; and
compiling the language strings into sentences, and ordering and concatenating the sentences into the text-based report, including compiling each of one or more pluralities of language strings into a single sentence.

24. A non-transitory computer-readable storage medium according to claim 23, wherein the receiving user input to add at least one additional vascular object or modifier operation comprises:
receiving user input to select a second vascular object or a modifier from a menu;
receiving user input to drag the selected second vascular object or modifier from the menu to a stage including the diagram;
receiving user input to drop the selected second vascular object or modifier onto the stage; and
snapping the selected second vascular object or modifier to one of the number of points on the first vascular object.

25. A non-transitory computer-readable storage medium according to claim 24, wherein the snapping operation comprises:
determining a snap-to point from the number of points on the first vascular object based upon at least one predefined characteristic restriction imposed by the selected second vascular object or modifier; and
snapping the selected second vascular object or modifier to the determined snap-to point.

26. A non-transitory computer-readable storage medium according to claim 24, wherein the receiving user input to add operation includes receiving user input to add a second vascular object, the selected second vascular object comprising a child vascular object and the first vascular object comprising a parent vascular object, the parent vascular object including a pair of sides, and wherein the snapping operation comprises:
determining an angle attribute of the child vascular object;
determining a side of the parent vascular object to which the child vascular object snaps; and
snapping the child vascular object proximate to the determined side of the parent such that the child vascular object extends from the determined side.

27. A non-transitory computer-readable storage medium according to claim 24, wherein the receiving user input to add operation includes receiving user input to add a modifier including:
snapping the modifier to the first vascular object from which the modifier depends, the number of points on the first vascular object including a finite plurality of interpretable points along a length of, and proximate each of a pair of sides of, the vascular object;
framing a shape of the modifier by a series of consecutive points on the vascular object; and
fitting a stock visual representation of the modifier to the series of consecutive points framing the shape of the modifier to thereby form-fit the modifier to the vascular object.

28. A non-transitory computer-readable storage medium according to claim 23, wherein the receiving user input to manipulate operation includes increasing or decreasing a curvature of the vascular object.

29. A non-transitory computer-readable storage medium according to claim 23, wherein the determining operation comprises for at least one vascular object added to the diagram of the vascular system:
determining a position attribute, a length attribute and an angle attribute associated with the vascular object, the position, length and angle attributes defining a direction of the vascular object; and
determining a name attribute associated with the vascular object based upon the direction of the vascular object and at least one rule.

30. A non-transitory computer-readable storage medium according to claim 23, wherein the vascular objects of the diagram comprise vascular objects of a plurality of vascular object types, and wherein the computer-readable storage medium has computer-readable program code portions stored therein that in response to execution by the processor cause the processor to further perform the following operations:
assigning each vascular object of the diagram to a respective holder array, each holder array including an identifier for each vascular object assigned to the holder array, the identifier being linked to the attributes associated with a respective vascular object,
wherein the generating operation comprises generating a text-based report based upon the holder arrays and the attributes linked to the vascular object identifiers in the holder arrays.

31. A non-transitory computer-readable storage medium according to claim 23, wherein the assigning operation includes placing at least one supporting word at least one of before or after an attribute to thereby assign a language string to the attribute.

32. A non-transitory computer-readable storage medium according to claim 23, wherein the compiling operation includes compiling the language strings into sentences based upon at least one function to correct any grammatical errors and thereby increase grammatical accuracy of the sentences.

33. A non-transitory computer-readable storage medium according to claim 23, wherein the providing operation includes providing a diagram of a heart, the diagram including vascular objects comprising at least one vascular object representing at least one of a branch, a graft or a collateral, and at least one modifier depending from at least one vascular object, the at least one modifier representing at least one of a stent or an aberration.

* * * * *